United States Patent [19]
Sawhney et al.

[11] Patent Number: 6,121,341
[45] Date of Patent: Sep. 19, 2000

[54] REDOX AND PHOTOINITIATOR SYSTEMS FOR PRIMING AND IMPROVED ADHERENCE OF GELS TO SUBSTRATES

[75] Inventors: Amarpreet S. Sawhney, Lexington, Mass.; David A. Melanson, Hudson, N.H.; Chandrashekar P. Pathak, Lexington, Mass.; Jeffrey A. Hubbell, San Marino, Calif.; Luis Z. Avila, Arlington, Mass.; Mark T. Kieras, Newburyport, Mass.; Stephen D. Goodrich, Woburn, Mass.; Shikha P. Barman, Lowell, Mass.; Arthur J. Coury, Boston, Mass.; Ronald S. Rudowsky, Sudbury, Mass.; Douglas J. K. Weaver, Bedford, Mass.; Marc A. Levine, Fremont, Calif.; John C. Spiridigliozzi, Dedham, Mass.; Thomas S. Bromander, Andover, Mass.; Dean M. Pichon, Concord, Mass.; George Selecman, Marblehead, Mass.; David J. Nedder, Attleboro, Mass.; Bradley C. Poff, White Bear Lake, Minn.; Donald L. Elbert, Pasadena, Calif.

[73] Assignees: Board of Regents, The University of Texas System, Austin, Tex.; Focal, Inc., Lexington, Mass.

[21] Appl. No.: 08/973,077

[22] PCT Filed: Mar. 22, 1996

[86] PCT No.: PCT/US96/03834

§ 371 Date: Oct. 10, 1997

§ 102(e) Date: Oct. 10, 1997

[87] PCT Pub. No.: WO96/29370

PCT Pub. Date: Sep. 26, 1996

Related U.S. Application Data

[63] Continuation-in-part of application No. 08/410,037, Mar. 23, 1995, and a continuation-in-part of application No. 08/472,745, Jun. 7, 1995, and a continuation-in-part of application No. 08/478,104, Jun. 7, 1995.

[51] Int. Cl.[7] .................................. C08K 1/00; A61F 2/00
[52] U.S. Cl. ............................... 522/84; 522/85; 424/426; 424/443; 424/444; 424/445; 128/898; 525/54.1; 527/202
[58] Field of Search ...................... 424/426, 486, 424/489, 443, 444, 445, 448; 522/84, 85; 128/898; 527/202; 525/54.1

[56] References Cited

U.S. PATENT DOCUMENTS

| | | |
|---|---|---|
| 3,223,083 | 12/1965 | Cobey . |
| 3,438,374 | 4/1969 | Falb et al. . |
| 3,552,986 | 1/1971 | Bassemir et al. . |
| 3,939,049 | 2/1976 | Ratner et al. . |
| 4,179,304 | 12/1979 | Rossomando . |
| 4,303,066 | 12/1981 | D'Andrea . |
| 4,354,487 | 10/1982 | Oczkowski et al. . |
| 4,511,478 | 4/1985 | Nowinski et al. . |
| 4,741,872 | 5/1988 | De Luca et al. . |
| 4,768,523 | 9/1988 | Cahalan et al. . |
| 4,804,691 | 2/1989 | English et al. . |
| 4,826,945 | 5/1989 | Cohn et al. . |

(List continued on next page.)

FOREIGN PATENT DOCUMENTS

| | | |
|---|---|---|
| 0 370 646 A1 | 5/1990 | European Pat. Off. . |
| 0 610 731 A1 | 8/1994 | European Pat. Off. . |
| 0 634 140 A1 | 1/1995 | European Pat. Off. . |
| 0 635 276 A1 | 1/1995 | European Pat. Off. . |
| 2 668 060 A1 | 4/1992 | France . |
| 4402590 | 1/1994 | Germany . |
| 62-267762 | 5/1986 | Japan . |
| 5310808 | 5/1993 | Japan . |
| WO 93/17669 | 9/1993 | WIPO . |

OTHER PUBLICATIONS

Chen & Hoffman, "Novel Graft Copolymers Of A Temperature–Sensitive Polymer Grafted To A pH–Sensitive, Bioadhesive Polymer For Controlled Drug Delivery", *21st Annual Meeting Of The Society For Biomaterials* (1995).

Cima, et al., "Hepatocyte Responses To PEO–Tethered Carbohydrates Depend On Tether Conformation," *21st Annual Meeting Of The Society For Biomaterials* (1995).

Constancis, et al., "Colcys As Surgical Adhesives", *21st Annual Meeting Of The Society For Biomaterials* (1995).

Dumanian, et al., "A New Photopolymerizable Blood Vessel Glue that Seals Human Vessel Anastomoses Without Augmenting Thrombogenicity," *Plastic and Reconstructive Surgery,* 95:901 (1995).

(List continued on next page.)

*Primary Examiner*—Nathan M. Nutter
*Attorney, Agent, or Firm*—Arnall Golden & Gregory, LLP

[57] ABSTRACT

An impoved barrier or drug delivery system which is highly adherent to the surface to which it is applied is disclosed, along with methods for making the barrier. In the preferred embodiment, tissue is stained with a photoinitiator, then the polymer solution or gel having added thereto a defined amount of the same or a different photoinitiator is applied to the tissue. On exposure to light, the resulting system polymerizes at the surface, giving excellent adherence, and also forms a gel in the rest of the applied volume. Thus a gel barrier of arbitrary thickness can be applied to a surface while maintaining high adherence at the interface. This process is referred to herein as "priming". the polymerizable barrier materials are highly useful for sealing tissue surfaces and junctions against leaks of fluids. In another embodiment, "priming" can be used to reliably adhere preformed barriers to tissue or other surfaces, or to adhere tissue surfaces to each other. A first surface and a barrier, or another surface, are prestained with initiator, and a thin layer of gelable monomer containing initiator is placed between them. Strong adhesion is obtained between the two surfaces on gelation of the monomer. In a similar fashion, tissue surfaces can be adhered to each other in repair of wounds and formation of anastomoses. Methods for use of non-photochemical systems and combined chemical/photochemical systems are described.

14 Claims, 9 Drawing Sheets

U.S. PATENT DOCUMENTS

| | | |
|---|---|---|
| 4,846,165 | 7/1989 | Hare et al. |
| 4,938,763 | 7/1990 | Dunn et al. |
| 4,997,722 | 3/1991 | Adler. |
| 5,009,224 | 4/1991 | Cole. |
| 5,019,100 | 5/1991 | Hennink et al. |
| 5,067,961 | 11/1991 | Kelman et al. |
| 5,100,992 | 3/1992 | Cohn et al. |
| 5,104,957 | 4/1992 | Kelman et al. |
| 5,137,800 | 8/1992 | Neckers et al. |
| 5,147,698 | 9/1992 | Cole. |
| 5,156,613 | 10/1992 | Sawyer. |
| 5,160,745 | 11/1992 | De Luca et al. |
| 5,173,301 | 12/1992 | Itoh et al. |
| 5,177,120 | 1/1993 | Hare et al. |
| 5,201,764 | 4/1993 | Kelman et al. |
| 5,209,776 | 5/1993 | Bass et al. |
| 5,226,877 | 7/1993 | Epstein. |
| 5,278,200 | 1/1994 | Coury et al. |
| 5,296,627 | 3/1994 | Tang et al. |
| 5,308,887 | 5/1994 | Ko et al. |
| 5,332,475 | 7/1994 | Mechanic. |
| 5,332,802 | 7/1994 | Kelman et al. |
| 5,354,336 | 10/1994 | Kelman et al. |
| 5,372,585 | 12/1994 | Tiefenbrun et al. |
| 5,385,606 | 1/1995 | Kowanko. |
| 5,403,626 | 4/1995 | Kim et al. |
| 5,410,016 | 4/1995 | Hubbell et al. |
| 5,459,177 | 10/1995 | Miyakoshi et al. |
| 5,476,515 | 12/1995 | Kelman et al. |
| 5,480,427 | 1/1996 | Kelman et al. |
| 5,484,913 | 1/1996 | Stilwell et al. |
| 5,496,872 | 3/1996 | Constancis et al. |
| 5,508,317 | 4/1996 | Muller. |
| 5,512,091 | 4/1996 | Steiner. |
| 5,516,825 | 5/1996 | Montador. |
| 5,525,647 | 6/1996 | Eichmiller. |
| 5,527,864 | 6/1996 | Suggs et al. |
| 5,529,914 | 6/1996 | Hubbell et al. |
| 5,530,038 | 6/1996 | Yamamoto et al. |
| 5,531,707 | 7/1996 | Kers et al. |
| 5,531,709 | 7/1996 | Eykmann et al. |
| 5,540,677 | 7/1996 | Sinofsky. |
| 5,552,452 | 9/1996 | Khadem et al. |
| 5,554,665 | 9/1996 | Tateosian et al. |
| 5,561,157 | 10/1996 | Yu et al. |

OTHER PUBLICATIONS

Dupont, et al., "New Surgical Sealant (Glue) Based On Controlled Oxidized Collagen", *21st Annual Meeting Of The Society For Biomaterials* (1995).

Frenkel, et al., "A Collagen Bilayer Implant For Articular Cartilage Repair In A Rabbit Model", *21st Annual Meeting Of The Society For Biomaterials* (1995).

Gagnieu, et al., "Colcys: New Crosslinkable Atelocolagens: Synthesis And Physico–Chemical Properties Of Highly Grafted Polymers", *21st Annual Meeting Of The Society For Biomaterials* (1995).

Gershkovich, et al., "Post–Surgical Adhesion Prevention With Bioresorbable Gels Of Amine Modified Hyaluronic Acid", *21st Annual Meeting Of The Society For Biomaterials* (1995).

Hata, et al., "Enzymatic Polymerization Of 2–Hydroxyethylmethacrylate For Artificial Embolization", *The Third World Biomaterials Congress*, 301 (1988).

Herbert, et al., "Polytetramethylene Oxide Blended With Polyurethane Reduces Platelet Adhesion", *21st Annual Meeting Of The Society For Biomaterials* (1995).

Hsu, et al., "Study On Aqueous Polymerizations Of Vinyl Monomers Initiated By Metal Oxidant–Chelating Agent Redox Initiators", *J. Polymer Science: Part A: Polymer Chem.* 31:3213–3222 (1993).

Wata, et al., "Solidifying Liquid With Novel Initiation System For Detachable Balloon Catheters", *Biomaterials* 13(13):891–896 (1992).

Kobayashi, et al., "Water–curable and biodegradable prepolymers," *J. Biom. Mat. Res.* 25:1481–1494 (1991).

McPherson, et al., "Scaling Analysis Of The Prevention Of Protein Adsorption By Grafted Peo Chains", *21st Annual Meeting Of The Society For Biomaterials* (1995).

Miller, et al., "Prevention Of Post–Surgical Tendon Adhesions Using Hyaluronic Acid Systems", *21st Annual Meeting Of The Society For Biomaterials* (1995).

Moore, et al., "An Injectable Biodegradable Drug Delivery System Based On Acrylic Terminated Poly(c–Caprolactone)", *21st Annual Meeting Of The Society For Biomaterials* (1995).

Mouritzen, et al., "The Effect Of Fibrin Glueing To Seal Bronchial And Alveolar Leakages After Pulmonary Resections And Decortications", *Eur. J. Cardio–thorac Surg.* 7:75–80 (1993).

Pemberton & Johnson, "Polymerization of Vinyl Acetate Using Visible Radiation and a Dye–Reducing Agent Sensitizer," *Polymer* 25: 536 (1984).

Pemberton & Johnson, "Polymerization of Vinyl Acetate Using Visible Radiation and a Dye–Reducing Agent Sensitizer: 2. Kinetic Studies and Polymerization Mechanism," *Polymer* 25: 543 (1984).

Rimpler, "Gluing—A Challenge In Surgery" *Int. J. Adhesion and Adhesives* 16: 17–20 (1996).

Sawhney, et al., "Optimization of photopolymerized bioerodible hydrogel properties for adhesion prevention," *J. Biomed. Mats. Res.* 28:831–838 (1994).

Sierra, et al., "Skullbase Cerebrospinal Fluid Leakage Control With A Fibrin–Based Composite Tissue Adhesive", *21st Annual Meeting Of The Society For Biomaterials* (1995).

Tardy, et al., "New Surgical Sealant(Glue) Based On Controlled Oxidized Collagen: Design And Physico–Chemical Characterization", *21st Annual Meeting Of The Society For Biomaterials* (1995).

Tiollier, et al., "Colcys As Surgical Adhesives: In Vivo Characterization And Biocompatibility", *21st Annual Meeting Of The Society For Biomaterials* (1995).

Tiollier, et al., "Novel Developments Of Collagen/Gelatin Surgical Adhesives For Surgical For Surgical Soft Tissue Applications", *21st Annual Meeting Of The Society For Biomaterials* (1995).

Tomizawa, et al., "Polypoxy Compound Cross–Linked Cotton Type Collagen Hemostat", *21st Annual Meeting Of The Society For Biomaterials* (1995).

Truong, et al., "In Vitro Conditions For Accelerated Hydrolysis Of Bioabsorbable Fibers", *21st Annual Meeting Of The Society For Biomaterials* (1995).

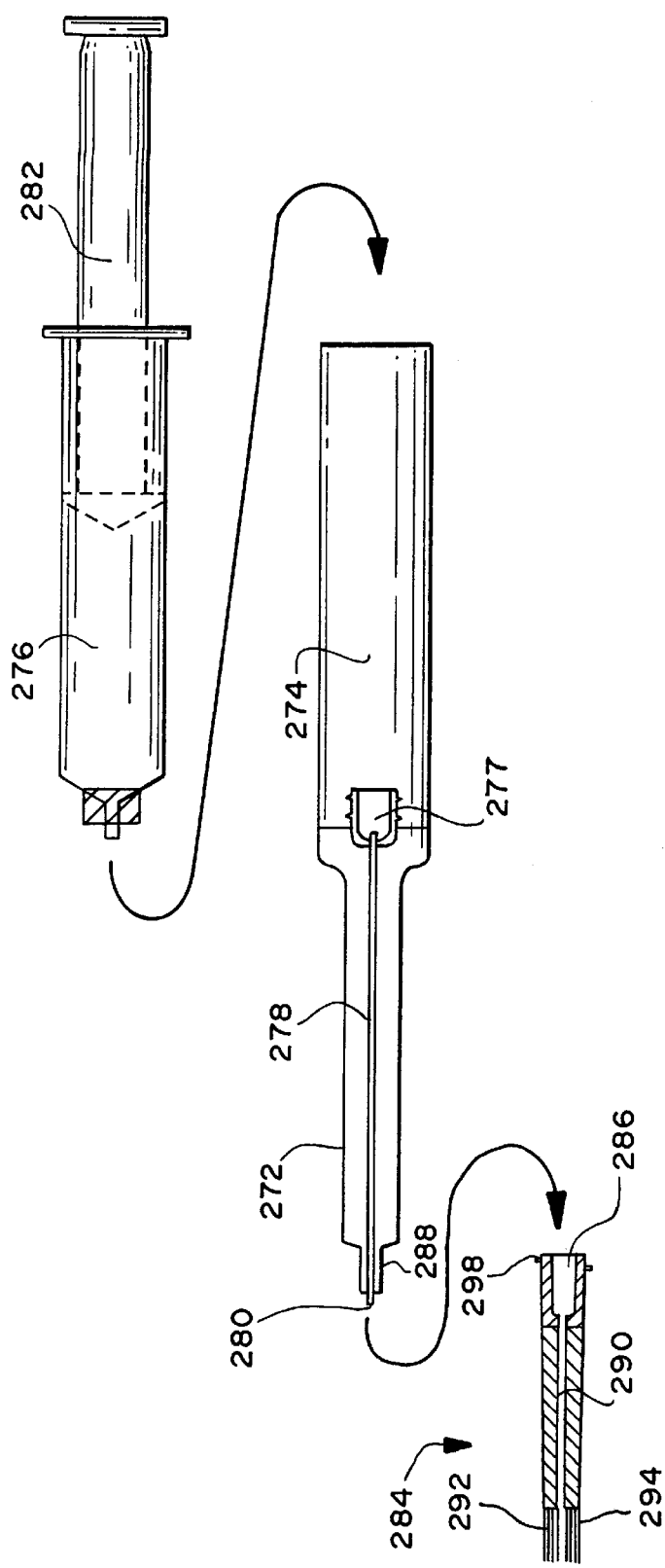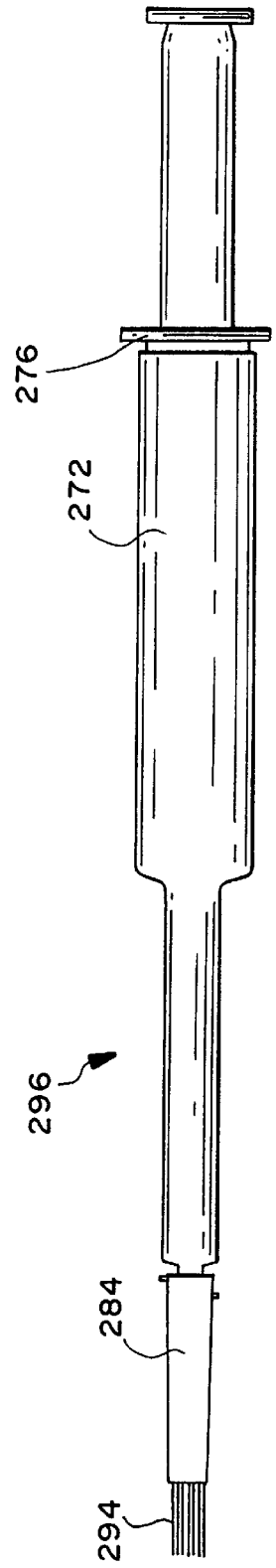
FIG. 9
FIG. 10

REDOX AND PHOTOINITIATOR SYSTEMS FOR PRIMING AND IMPROVED ADHERENCE OF GELS TO SUBSTRATES

Priority is claimed under 35 U.S.C. §119 to PCT/US 96/03834, filed Mar. 22, 1996, which is a continuation-in-part of U.S. Ser. No. 08/410,037, filed Mar. 23, 1995; U.S. Ser. No. 08/472,745, filed Jun. 7, 1995; and U.S. Ser. No. 08/478,104, filed Jun. 7, 1995.

BACKGROUND OF THE INVENTION

The present invention relates to methods and compositions for improving the adherence of polymer gels to surfaces, especially tissue surfaces; devices for applying the compositions and gels; and general methods for sealing surfaces with gels for therapeutic benefit.

Locally polymerized gels have been used as barriers and drug delivery devices for several medical conditions. Adherence of the formed gel to the tissue can be a problem, especially under surgical conditions, where the tissue surface to be treated is typically wet, and may further be covered with blood, mucus or other secretions. Hubbell and co-workers have described two methods for photopolymerizing gels in contact with tissue surfaces. In U.S. Pat. No. 5,410,016, hereby incorporated by reference, application of biodegradable macromers to tissue, followed by photopolymerization to form a gel, is described. Two methods for photopolymerizing gels are described. In "bulk" polymerization, a suitable photoinitiator and accessory reagents are solubilized or dispersed in a solution of gelling macromers. On application of light, the entire solution volume crosslinks to form a gel which acts as a local barrier or drug depot. These gels have substantial adherence to most surfaces, including tissue surfaces which are merely moist. However, if a confounding layer of fluid is present on the surface when the macromer/initiator solution is applied, then the gel may delaminate from the surface after its formation.

An alternative way of form a gel layer on a surface, as also described in U.S. Ser. No. 08/024,657, which is hereby incorporated by reference, is called the "interfacial" method. In this method, the surface to be coated is treated with a photoinitiator which adsorbs or absorbs to the surface. After washing away excess, unabsorbed photoinitiator, a polymerizable macromer solution is applied to the surface. On exposure to light, polymerization is initiated at the surface, and progresses outward into the solution to the limit of diffusion of the photoinitiator-generated radicals during their lifespan. Coating thicknesses of up to about 500 micrometers (microns) are routinely obtained. Since they are in effect "grown" from the tissue surface, such gel layers have excellent adhesion to the tissue surface under difficult conditions, including the presence of thin layers of fluid adherent to the surface. The limited thickness of such interfacial gels is desirable in some circumstances, but represents a major limitation where gels of substantially greater thickness than 500 microns are required, for example, for use in drug delivery, or in forming an effective barrier between the tissue surface and its surroundings.

In addition to the photopolymerizable gels described by Hubbell et al (WO 93/17669) and Sawhney et al, (*J. Biomed. Mats. Res.* 28, 831–838, 1994), systems for forming drug delivery depots or barriers on surfaces include the polymers described in U.S. Pat. No. 4,938,763 to Dunn, et al., U.S. Pat. Nos. 5,100,992 and 4,826,945 to Cohn et al, U.S. Pat. Nos. 4,741,872 and 5,160,745 to De Luca et al, and U.S. Pat. No. 4,511,478 to Nowinski et al. Use of preformed barrier materials such as Goretex™ membrane (W. L.Gore) has been described in the literature.

Although all of these materials are suitable for application to tissue and other substrates, adhesion is in many cases limited, or in the case of the preformed barrier materials, essentially non-existent.

It is therefore an object of the present invention to provide methods and compositions for enhancing the adhesion of polymeric materials to tissue surfaces and other substrates.

It is a further object of the present invention to provide methods and compositions for increasing the thicknesses of polymeric materials which can be "tethered" to a tissue surface or other substrates.

It is a further object of the present invention to provide improved initiator systems for the formation of gels on tissues and other surfaces.

It is a further object of the present invention to provide improved methods and new medical indications for the sealing and coating of tissue.

It is a further object of the present invention to provide devices suitable for performing these operations.

SUMMARY OF THE INVENTION

An improved barrier, coating or drug delivery system which is highly adherent to the surface to which it is applied is disclosed, along with methods for making the barrier. In the preferred embodiment, tissue is stained with a photoinitiator, then the polymer solution or gel in combination with a defined amount of the same or a different photoinitator is applied to the tissue. On exposure to light, the resulting system polymerizes at the surface, giving excellent adherence, and also forms a gel throughout the illuminated volume. Thus a gel barrier or coating of arbitrary thickness can be applied to a surface while maintaining high adherence at the interface. This process is referred to herein as "priming". The polymerizable barrier materials are highly useful for sealing tissue surfaces and junctions against leaks of fluids. In the examples described below, the fluids are air and blood; however, the principle is also applicable to other fluids, including bowel contents, urine, bile, cerebrospinal fluid, vitreous and aqueous humors and other fluids whose migration within a living organism must be contained.

In another embodiment, "priming" can be used to reliably adhere preformed barriers or coatings to tissue or other surfaces, or to adhere tissue surfaces to each other. A first surface and a preformed barrier or coating, or another surface, are prestained with initiator, and a thin layer of polymerizable monomer containing initiator is placed between them. Strong adhesion is obtained between the two surfaces on polymerization of the monomer. In a similar fashion, tissue surfaces can be adhered to each other in repair of wounds and formation of anastomoses.

The priming method is suitable for any mode of polymerization. While especially effective in photopolymerization, chemical or thermal polymerization can also be accomplished by this method. Further, an enhancement of photoinitiation can be achieved by adding suitable redox initiation components to the system, providing a new form of light-controlled chemically accelerated polymerization reaction, especially effective in the presence of blood.

According to one embodiment, the invention provides a device for dispensing a fluid to a tissue surface in a medical setting, having a proximal portion operable by a user of the device and a distal portion having an applicator outlet for addressing the tissue surface. The devices is characterized in that it includes at least two chambers for receiving fluids to be dispensed to the tissue surface and conduits connecting each chamber to an applicator outlet at the distal portion of the device. The device also includes an optical emitter at the distal portion for applying light to the fluid at the tissue surface.

According to another embodiment, the invention provides a device for dispensing a fluid to a tissue surface as described above, characterized in that it includes at least two chambers for receiving fluids to be dispensed to the tissue surface and conduits connecting each chamber to an applicator outlet at the distal portion of the device, a first dispensing mechanism activating dispensing of fluid from the first chamber to the tissue surface, operably linkable to a trigger at the proximal portion, and a second dispensing mechanism activating dispensing of fluid from the second chamber to the tissue surface, operably linkable to a trigger at the proximal portion.

According to another embodiment, the invention provides a dispensing adapter for use in a medical setting. The adapter operates by attachment to a device having a reservoir for containing a fluid to be dispensed to a tissue surface and a fluid outlet, and is characterized in that it is fastenable to the device and removable therefrom, and includes a conduit having a proximal end connectable in a fluid-tight manner to the fluid outlet of the device, a distal end defining a adapter fluid outlet, and a spreading member at the distal end adapted to spread fluid dispensed from the adapter fluid outlet on the tissue surface.

The invention also provides a dispensing adapter for use in a medical setting by attachment to a device having a reservoir for containing a fluid to be dispensed to a tissue surface and a fluid outlet. The dispensing adapter is characterized in that it includes an opaque chamber for containing the device, an opaque conduit having a proximal end connectable in a fluid-tight manner to the fluid outlet of the device, and a distal end defining a adapter fluid outlet

BRIEF DESCRIPTION OF THE DRAWINGS

FIGS. 1a and 1b are schematic drawings of a two-fluid-one-dispenser version of an application device, in which FIG. 1a is a longitudinal schematic cross-section and FIG. 1b is a view from the proximal end of the device.

FIG. 9 illustrates schematically a dispenser arrangement according to another embodiment of the invention.

FIG. 10 illustrates schematically the arrangement of FIG. 9, as assembled.

DETAILED DESCRIPTION OF THE INVENTION

Figures 1A, 1B:
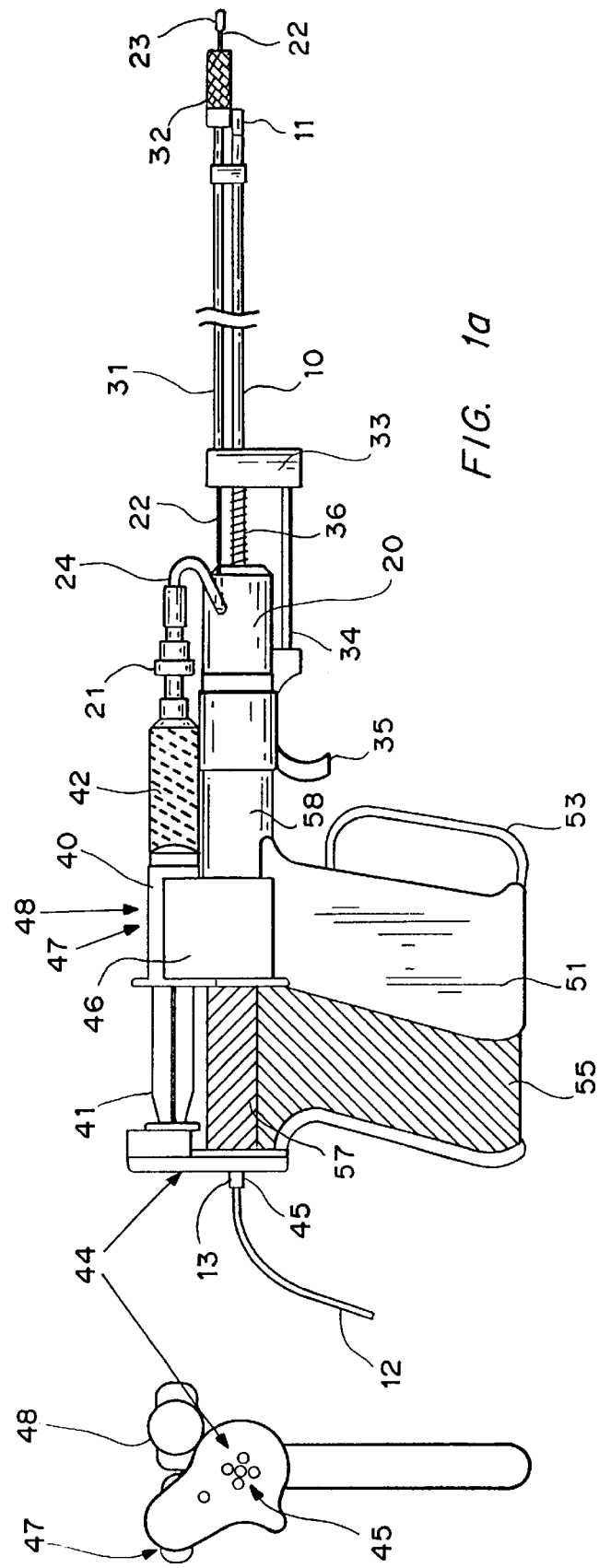

As described herein, one or more initiators are applied to a surface to form an absorbed layer. "Absorbed" is used herein to encompass both "absorbed" and "adsorbed". A solution of polymerizable molecules, referred to herein as "monomers", is then applied.

Methods

There are several embodiments of the method described herein.

In its simplest embodiment, one or more initiators or components of an initiation system are applied directly to the surface, and the unabsorbed excess is optionally removed by washing or blotting. The initiator solution may further contain one or more polymerizable monomers, and other useful formulating ingredients, including accelerators, co-initiators, sensitizers, and co-monomers. Then a liquid containing polymerizable monomers in combination with one or more initiators or components of an initiation system, which may be the same as or different from that absorbed in the first step, is applied. The system, if not self-polymerizing, is then stimulated to polymerize, for example by application of an appropriate wavelength of light.

The priming and monomer-application steps can also be combined. For example, if excess initiator is not removed before monomer addition, then subsequent application of monomer will result in mixture of initiator into the monomer layer. Similarly, if the monomer layer contains an initiator with a high affinity for the surface, then it is possible to apply a monomer layer containing initiator, and wait an appropriate time to allow preferential absorption of the initiator to the surface, to achieve the same effect.

All of these methods may collectively be described as application of the monomer in an "initiating-incorporating manner", encompassing any means of application and mixing which results in both an absorbed layer of initiator, and a layer of monomer incorporating an initiator, being present on a surface to be coated.

The initiators may be chemical, photochemical, or a combination thereof. With non-photochemical systems, a reductant component and an oxidant component may be present in the two parts of the solution, i.e., in the priming layer and the coating layer.

Alternatively, a two-step process can be used to form polymers, especially bioabsorbable hydrogels on tissue. In the first step the tissue is treated with an initiator or a part of an initiator system for the polymerization of olefinic (e.g. acrylic) or other functional monomers, optionally with monomer in the priming solution. This provides an activated tissue surface. In the second step, monomer(s) and, if appropriate, the remainder of an initiator system, are together placed in contact with the activated tissue, resulting in polymerization on the tissue. An example of such a system is the combination of a peroxygen compound in one part, and a reactive ion, such as a transition metal, in another.

This process of spontaneous polymerization does not require the use of a separate energy source. Moreover, since the process of polymerization is initiated when part one contacts part two, there are no "pot life" issues due to initiation of polymerization. If desired, part one or part two can contain dyes or other means for visualizing the hydrogel coating.

An example of a system that can be used in this method is the spontaneous "contact" initiator systems such as those found in two part "acrylic structural adhesives". All components of the materials used as described herein, however, must display biocompatibility as well as the ability to spontaneously polymerize on tissue. The use of tributyl borane for this purpose is illustrated here. These systems can markedly simplify the delivery of gel to tissue, especially in areas hard to reach or hold for a photochemical system. The delivery system can be much simpler. Moreover, it has been discovered that a two-part chemical system such as a redox system and especially one based on peroxygen, can be used to chemically enhance the curing of a photochemical system, thereby combining the control of a photochemical system with the ability of a chemical system to overcome colored impurities, such as blood.

Compositions

MONOMERS

Any monomer capable of being polymerized to form a surface coating can be used. The monomers may be small molecules, such as acrylic acid or vinyl acetate; or they may be larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat. Nos. 4,741,872 and 5,160,745 to De Luca et al., or U.S. Pat. No. 5,410,016 by Hubbell et al. Properties of the monomer, other than polymerizability, will be selected according to the use, using principles as known in the art. There is an extensive literature on the formulation of polymerizable coating materials for particular applications; these formulae can readily be adapted to use the improved adherence-promoting polymerization system described herein with little experimentation.

In the particular application area of coating of tissues, cells, medical devices, and capsules, formation of implants for drug delivery or as mechanical barriers or supports, and other biologically related uses, the general requirement of the coating materials are biocompatibility and lack of toxicity. For all biologically-related uses, toxicity must be low or absent in the finished state for externally coated non-living materials, and at all stages for internally-applied materials. Biocompatibility, in the context of biologically-related uses, is the absence of stimulation of a severe, long-lived or escalating biological response to an implant or coating, and is distinguished from a mild, transient inflammation which accompanies implantation of essentially all foreign objects into a living organism.

The monomer solutions should not contain harmful or toxic solvents. Preferably, the monomers are substantially soluble in water to allow their application in a physiologically-compatible solution, such as buffered isotonic saline. Water-soluble coatings may form thin films, but more preferably form three-dimensional gels of controlled thickness.

It is especially preferable in cases involving implants that the coating formed be biodegradable, so that it does not have to be retrieved from the body. Biodegradability, in this context, is the predictable disintegration of an implant into small molecules which will be metabolized or excreted, under the conditions normally present in a living tissue.

Preferred monomers are the photopolymerizable, biodegradable, water-soluble macromers described by Hubbell et al. in U.S. Pat. No. 5,410,016, the teachings of which are incorporated herein. These monomers are characterized by having at least two polymerizable groups, separated by at least one degradable region. When polymerized in water, they form coherent gels which persist until eliminated by self-degradation. In the most preferred embodiment, the macromer is formed with a core of a polymer which is water soluble and biocompatible, such as the polyalkylene oxide polyethylene glycol, flanked by hydroxy acids such as lactic acid, having coupled thereto acrylate groups. Preferred monomers, in addition to being biodegradable, biocompatible, and non-toxic, will also be at least somewhat elastic after polymerization or curing. Elasticity, or repeatable stretchability, is often exhibited by polymers with low modulus. Brittle polymers, including those formed by polymerization of cyanoacrylates, are not generally effective in contact with biological soft tissue.

It has been determined that monomers with longer distances between crosslinks are generally softer, more compliant, and more elastic. Thus, in the polymers of Hubbell, et al., increased length of the water-soluble segment, such as polyethylene glycol, tends to give more elastic gel, and these tend to adhere better, especially under stretching (as when applied to lung). Molecular weights in the range of 10,000 to 35,000 of polyethylene glycol are preferred for such applications, although ranges from 3,000 to 100,000 are useful.

In the discussion below and the examples, monomers of this kind, also called macromers, are often designated by a code of the form xxKZn. "xxK" represents the molecular weight of the backbone polymer, which is polyethylene glycol unless otherwise stated, in thousands of daltons. Z designates the biodegradable linkage, where L is for lactic acid, G is for glycolic acid, C is for caprolactone, and TMC is for trimethylenecarbonate. N is the average number of degradable groups in the block. The molecules are terminated with acrylic acid groups, unless otherwise stated; this is sometimes also indicated by the suffix A2.

INITIATORS

The term "initiator" is used herein in a broad sense, in that it is a composition which under appropriate conditions will result in the polymerization of a monomer. Materials for initiation may be photoinitiators, chemical initiators, thermal initiators, photosensitizers, co-catalysts, chain transfer agents, and radical transfer agents. All initiators known in the art are potentially suitable for the practice of the priming technique. The critical property of an initiator is that the polymerization will not proceed at a useful rate without the presence of the initiator.

The "priming" initiator must adhere sufficiently to the surface to be coated to provide a local source of initiation of the reaction with the particular monomers to be applied. The initiator must also not be toxic when used in biologically-related applications, at least in the amounts applied. The initiator is preferably a photoinitiator. In discussing photoinitiators, a distinction may be drawn between photosensitizers and photoinitiators—the former absorb radiation efficiently, but do not initiate polymerization well unless the excitation is transferred to an effective initiator or carrier. Photoinitiators as referred to herein include both photosensitizers and photoinitiators, unless otherwise noted.

Photoinitiators provide important curing mechanisms for addition polymerization, and especially for curing of ethylenically-unsaturated compounds, such as vinylic and acrylic-based monomers. Any of the photoinitiators found in the art may be suitable, if they adhere to the particular surface. Examples of photo-oxidizable and photo-reducible dyes that may be used to initiate polymerization include acridine dyes, for example, acriblarine; thiazine dyes, for example, thionine; xanthine dyes, for example, rose Bengal, and phenazine dyes, for example, methylene blue. Other initiators include camphorquinones and acetophenone derivatives. Photoinitiation is a preferred method of polymerizing the coatings and adhesives of the invention.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. In an alternative mechanism, the initiator splits into radical-bearing fragments which initiate the reaction. Preferred dyes for use with these materials include eosin dye and initiators such as 2,2-dimethyl-2-phenylacetophenone, 2-methoxy-2-phenylacetophenone, Darocur™ 2959, Irgacurep™ 651 and camphorquinone. Using such initiators, copolymers may be polymerized in situ by long wavelength ultraviolet light or by light of about 514 nm, for example.

A preferred photoinitiator for biological use is Eosin Y, which absorbs strongly to most tissue and is an efficient photoinitiator.

It is known in the art of photopolymerization to use a wavelength of light which is appropriate for the activation of a particular initiator. Light sources of particular wavelengths or bands are well-known.

Thermal polymerization initiator systems may also be used. Systems that are unstable at 37° C. and initiate free radical polymerization at physiological temperatures include, for example, potassium persulfate, with or without tetramethyl ethylenediamine; benzoyl peroxide, with or without triethanolamine; and ammonium persulfate with sodium bisulfite. Other peroxygen compounds include t-butyl peroxide, hydrogen peroxide and cumene peroxide. As described below, it is possible to markedly accelerate the rate of a redox polymerization by including metal ions in the solution, especially transition metal ions such as the ferrous ion. It is further shown below, that a catalysed redox reaction can be prepared so that the redox-catalysed polymerization is very slow, but can be speeded up dramatically by stimulation of a photoinitiator present in the solution.

A further class of initiators is provided by compounds sensitive to water, which form radicals in its presence. An example of such a material is tri-n-butyl borane, the use of which is described below.

REDOX INITIATORS

Metal ions can be either an oxidizer or a reductant in systems including redox initiators. For example, in some examples below, ferrous ion is used in combination with a peroxide to initiate polymerization, or as parts of a polymerization system. In this case the ferrous ion is serving as reductant. Other systems are known in which a metal ion acts as oxidant. For example, the ceric ion (4+ valence state of cerium) can interact with various organic groups, including carboxylic acids and urethanes, to remove an electron to the metal ion, and leaving an initiating radical behind on the organic group. Here the metal ion acts as an oxidizer. Potentially suitable metal ions for either role are any of the transition metal ions, lanthanides and actinides, which have at least two readily accessible oxidation states. Preferred metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous.

CO-INITIATORS AND COMONOMERS

Any of the compounds typically used in the art as radical generators or co-initiators in photoinitiation may be used. These include co-catalysts or co-initiators such as amines, for example, triethanolamine, as well as other trialkyl amines and trialkylol amines; sulfur compounds; heterocycles, for example, imidazole; enolates; organometallics; and other compounds, such as N-phenyl glycine.

Co-monomers can also be used. They are especially useful when the monomer is a macromolecule, as in Example 1 below; in that case, any of the smaller acrylate, vinyl or allyl compounds can be used. Comonomers can also act as accelerators of the reaction, by their greater mobility, or by stabilizing radicals. Of particular interest are N-vinyl compounds, including N-vinyl pyrrolidone, N-vinyl acetamide, N-vinyl imidazole, N-vinyl caprolactam, and N-vinyl formamide.

SURFACTANTS, STABILIZER, AND PLASTICIZERS

Other compounds can be added to the initiator and/or monomer solutions. Surfactants may be included to stabilize any of the materials, either during storage or in a form reconstituted for application. Similarly, stabilizers which prevent premature polymerization may be included; typically, these are quinones, hydroquinones, or hindered phenols. Plasticizers may be included to control the mechanical properties of the final coatings. These are also well-known in the art, and include small molecules such as glycols and glycerol, and macromolecules such as polyethylene glycol.

DRUGS

Biologically active materials may be included in any of the coatings described herein, as ancillaries to a medical treatment (for example, antibiotics) or as the primary objective of a treatment (for example, a gene to be locally delivered). A variety of biologically active materials may be included, including passively-functioning materials such as hyaluronic acid, as well as active agents such as growth hormones. All of the common chemical classes of such agents are included: proteins (including enzymes, growth factors, hormones and antibodies), peptides, organic synthetic molecules, inorganic compounds, natural extracts, nucleic acids, lipids and steroids, carbohydrates, glycoproteins, and combinations thereof.

SURFACES TO BE TREATED

Surfaces to be coated include biologically-related surfaces of all kinds. In particular, any tissue or cell surface is contemplated, as well as the surface of a device to be used in the body or in contact with bodily fluids. A coating may be applied to the surface of any of these, in an amount effective to improve tenacity of adherence. Moreover, the technique may be used to adhere surfaces to each other. For example, wounds in living tissue may be bonded or sealed using this technique or preformed medical appliances may be bonded to tissue. Examples of such applications are grafts, such as vascular grafts; implants, such as heart valves, pacemakers, artificial corneas, and bone reinforcements; supporting materials, such as meshes used to seal or reconstruct openings; and other tissue-non-tissue interfaces. A particularly important class of tissue surfaces is those which are friable, and therefore will not support sutures well. Adherent coatings can seal the suture lines, support sutured areas against mechanical stress, or substitute entirely for sutures when mechanical stress is low. Examples of such situations include vascular anastomosis, nerve repair, repair of the cornea or the cochlea, and repair of the lung, liver, kidney and spleen.

The priming technique can also be used on non-tissue surfaces in general, where useful bonds may be formed between similar or dissimilar substances, and solid or gel coatings are tightly adhered to surfaces. In particular, a pre-formed gel, or other fragile material, may be tightly adhered to a supporting material by this method.

The priming method of this invention is advantageous because it can be used to coat and or to bond together any of a wide variety of surfaces. These include all surfaces of the living body, and surfaces of medical devices, implants, wound dressings and other body-contacting atrificial or natural surfaces. These include, but are not limited to, at least one surface selected from the following: a surface of the respiratory tract, the meninges, the synovial spaces of the body, the peritoneum, the pericardium, the synovia of the tendons and joints, the renal capsule and other serosae, the dermis and epidermis, the site of an anastomosis, a suture, a staple, a puncture, an incision, a laceration, or an apposition of tissue, a ureter or urethra, a bowel, the esophagus, the patella, a tendon or ligament, bone or cartilage, the stomach, the bile duct, the bladder, arteries and veins; and devices such as percutaneous catheters (e.g. central venous catheters), percutaneous cannulae (e.g. for ventricular assist devices), urinary catheters, percutaneous electrical wires, ostomy appliances, electrodes (surface and implanted), and implants including pacemakers, defibrillators, and tissue augmentations.

BIOLOGICALLY ACTIVE AGENTS

Biologically active substance can be incorporated into the polymer. Examples of useful biologically active substances include proteins (including enzymes, growth factors, hormones and antibodies), peptides, organic synthetic molecules including antibiotics, inorganic compounds, natural extracts, nucleic acids including genes, antisense nucleotides, and triplex forming agents, lipids and steroids, carbohydrates, including hyaluronic acid and heparin, glycoproteins, and combinations thereof.

Methods of Treatment

Generally, any medical condition which requires a coating or sealing layer may be treated by the methods described herein to produce a coating with better adherence. In the examples below, lung tissue is sealed against air leakage after surgery using the priming technique. Likewise, wounds may be closed; leakage of blood, serum, urine, cerebrospinal fluid, air, mucus, tears, bowel contents or other bodily fluids may be stopped or minimized; barriers may be applied to prevent post-surgical adhesions, including those of the pelvis and abdomen, pericardium, spinal cord and dura, tendon and tendon sheath. The technique may also be useful for treating exposed skin, in the repair or healing of incisions, abrasions, burns, inflammation, and other conditions requiring application of a coating to the outer surfaces of the body. The technique is also useful for applying coatings to other body surfaces, such as the interior or exterior of hollow organs, including blood vessels. In particular, restenosis of blood vessels or other passages can be treated. The techniques can also be used for attaching cell-containing matrices, or cells, to tissues, such as meniscus or cartilage.

GENERAL SEALING OF BIOLOGICAL TISSUES

As shown in the examples below, the priming method of polymerization is especially effective in the sealing of biological tissues to prevent leakage. However, the examples also demonstrate that a degree of sealing can be achieved with photopolymerizable systems without the improvement of priming the tissue with photopolymerizing initiator. There have been numerous attempts to reliably seal tissue with a number of materials, including most prominently cyanoacrylates and fibrin glues. None of these prior art techniques has been entirely satisfactory.

Cyanoacrylates, which polymerize on exposure to moisture, and can be accelerated by amines, are very "stiff" once polymerized. If there is any motion of the biological material, they tend to crack, and lose their self-cohesion and/or their adherence to tissue. Fibrin glues can be difficult to prepare, especially in the currently-preferred autologous version; they require enzymatic or toxic chemical means to be gelled or crosslinked; and they are rapidly degraded by native enzymes.

The range of uses of sealing or bonding materials in the body is very large, and encompasses many millions of potential uses each year. In cardiovascular surgery, uses for tissue sealants include bleeding from a vascular suture line; support of vascular graft attachment; enhancing preclotting of porous vascular grafts; stanching of diffuse nonspecific bleeding; anastomoses of cardiac arteries, especially in bypass surgery; support of heart valve replacement; sealing of patches to correct septal defects; bleeding after sternotomy; and arterial plugging. Collectively, these procedures are performed at a rate of 1 to 2 million annually. In other thoracic surgery, uses include sealing of bronchopleural fistulas, reduction of mediastinal bleeding, sealing of esophageal anastomoses, and sealing of pulmonary staple or suture lines. In neurosurgery, uses include dural repairs, microvascular surgery, and peripheral nerve repair. In general surgery, uses include bowel anastomoses, liver resection, biliary duct repair, pancreatic surgery, lymph node resection, reduction of seroma and hematoma formation, endoscopy-induced bleeding, plugging or sealing of trocar incisions, and repair in general trauma, especially in emergency procedures. In plastic surgery, uses include skin grafts, burns, debridement of eschars, and blepharoplasties (eyelid repair). In otorhinolaryngology (ENT), uses include nasal packing, ossicular chain reconstruction, vocal cord reconstruction and nasal repair. In opthalmology, uses include corneal laceration or ulceration, and retinal detachment. In orthopedic surgery, uses include tendon repair, bone repair, including filling of defects, and meniscus repairs. In gynecology/obstetrics, uses include treatment of myotomies, repair following adhesiolysis, and prevention of adhesions. In urology, sealing and repair of damaged ducts, and treatment after partial nephrectomy are potential uses. Sealing can also be of use in stopping diffuse bleeding in any of a variety of situations, including especially treatment of hemophiliacs. In dental surgery, uses include treatment of periodontal disease and repair after tooth extraction. Repair of incisions made for laparoscopy or other endoscopic procedures, and of other openings made for surgical purposes, are other uses. Similar uses can be made in veterinary procedures. In each case, appropriate biologically active components may be included in the sealing or bonding materials.

APPLICATION TECHNIQUES AND DEVICES

Both priming and polymer addition may be accomplished by simple dripping of material onto the surface to be coated. This can be accomplished using common devices such as a syringe, a pipet, or a hose, depending on scale. More uniform applications may be obtained using an applicator, such as a brush, a pad, a sponge, a cloth, or a spreading device such as a finger, a coating blade, a balloon, or a skimming device. These may further be used to rub the surface to improve penetration of the primer or the monomer, or to mix primer and monomer in situ on the surface. In large-scale applications, fluid layers may be applied with large-scale coating machinery, including roll coaters, curtain coaters, gravure and reverse gravure devices, and any of the coating devices known in the art.

Sprayers may be used at any scale, especially for lower-viscosity primers or polymerizable monomer layers.

Application techniques and devices may be combined, as in applying fluid from a syringe, and then rubbing it into the surface with a finger tip. Such operations may be repeated, as in applying drops of priming initiator; rubbing these into the surface with a brush; repeating this operation; adding monomer solution; rubbing it in; and finally applying additional layers of monomer before or during the application of curing means, such as light, heat, or slow release of peroxide radicals.

An additional application means which is required in many coating techniques described herein, and in particular in the preferred coating method which uses photoinitiation to cure the monomer, is a light source. For large-scale application, flood lamps and similar devices are useful. In small, localized applications, such as tissue sealing and coating, it may be preferable to use a localized source such as a fiber optic or light guide, which can project radiation of the appropriate wavelength onto the site to be treated to cause polymerization of the monomer. Also, a light emitter could be carried on a device, as a miniature bulb. A focused beam from a remote source could be suitable if, for example, the surface was exposed. In exposed surfaces, it is possible that ambient light could be sufficient to polymerize the coating, especially at high initiator levels.

Each of the applications means can be separate, so that a kit of application means could contain, for example, one or more reservoirs, one or more pads or brushes, and if required at least one light guide. The application means could also be combined in whole or in part. For example, a dripping device, such as a tube, could be combined with a spreading device, such as a brush. These could further be combined with a light guide. Such combination devices are especially desirable in treatment of living organisms, and especially humans, to maximize the simplicity of a procedure and the probability of correctly conducting it.

Thus, a combination device for conducting a primed photopolymerization in a biological or medical setting will contain at least the following elements:

a) one or more means for applying a fluid to a surface, selected from dripping means, irrigating means, spraying means, applicator pad means including brushes, balloons, fabrics and foams, and rigid surfaces, such as spatulas, for applying paste-like or highly viscous fluids;

b) one or more optional means for spreading or rubbing a fluid onto a surface, which may be brushes, pads, rigid or semi-rigid protuberances, and which may be the same or different as the fluid-application means;

c) one or more reservoirs, or connecting conduits for receiving the contents of reservoirs into the device, for a primer, a monomer solution, and/or a combination thereof;

d) light-delivery means, which may be a fiber optic, a light guide, a focused remote beam, or a locally-deployed light source, such as a miniature lamp;

e) a proximal end adapted to be held by the person administering the treatment, optionally further including means for selection among the one or more application means, spreading means, reservoir means, and light-delivery means (i.e., switching means); and f) a distal end or ends, optionally adapted to be sterilizable, from which the one or more fluids are dispensed.

Other options for the device include metering means for the fluids, so that a controlled amount may be dispensed, or a controlled pressure may be maintained; feedback devices, such as optical viewers and indicators of function; and interlocks to correctly sequence the application procedure, or to insure dispensing of the required amounts of initiator, monomer, and light or other polymerization stimulator.

Many devices and arrangements can be constructed that meet these requirements. One embodiment of such a device is illustrated in FIGS. 1a and 1b, in which FIG. 1a is a longitudinal schematic cross-section, and FIG. 1b is a view from the proximal end of a two-fluid-one-dispenser version.

In FIG. 1a, a main shaft 10, of which the distal end is shown, carries light from a remote light source (not shown) coupled into an optical fiber or fibers 12 passing into the shaft through a bushing or strain-relief member 13 at the proximal end of the device, and through the axis of the device to a distal emission element 11. The emission element contains appropriate optical elements to distribute the light onto the site where polymerization is to occur. These may be as simple as a window, but may include other arrangements known in the art to distribute the light, including diffusers, lenses or gratings, and collimating stops.

Syringes 47, 48 (see also FIG. 1b) with check valves 21 are provided for the delivery of fluids via a connector 24 through a bifurcation in the body extension 20 to a fluid delivery conduit 22, the ends of which are shown. The fluid delivery conduit may have a specialized applicator tip 23, such as a spray nozzle, or may be smooth for simple delivery of fluid by dripping. The fluid delivery conduit is optionally surrounded by a slidable tube 31 carrying a spreading device 32, which is connected by a block 33 which slides on the main shaft 10. The sliding block 33 slides the telescoping tube 31 on the fluid delivery conduit 22. The block is connected by a connecting rod 34 to a trigger mechanism 35, which is used to slide the spreading device 32 either distally of the emission element 23, or proximately of it, depending on the step of the priming operation. The trigger 35 may also optionally be provided with spring tensioners 36 or latches or detents for controlling position (not illustrated).

A syringe barrel 40 containing a fluid to be delivered 42 is fitted with a plunger 41. The plunger is selectively contactable by a plunger driver 44, which may be rotated about the device axis 45 to drive either of the two syringes 47, 48 shown in FIG. 1b. The syringes are held on the device by a clamp 46.

The plunger driver 44 is connected to a freely sliding rod 57 which can slide into a recess 58 in the device under the influence of slidable hand grip 55, which slides into handle 51. A finger guard 53 is provided for convenience.

In operation, the device is used as follows. With the spreading device 32 retracted to the proximal position, the plunger driver 44 is positioned over the filled initiator (primer) syringe 47, and by compressing the slidable portion of the hand grip 55 into the handle 51, fluid is dripped from delivery conduit 22 onto the target area. Then the spreading device is moved to the distal position and is used, by movement of the device as a whole by the operator, to spread the initiator priming solution over the entire target area. Alternatively, the spreading device may be in the distal position during primer delivery, so that the fluid is distributed by it.

Next, the spreading device is optionally retracted, and the driver 44 is moved to drive syringe 48, which contains a solution with monomer, initiator, carrier amine, and other ingredients. The monomer solution is dripped onto the target region, the spreader is advanced, and the monomer is rubbed into and distributed on the surface. Optionally, the spreader is retracted and further monomer is applied to the surface, optionally with the aid of the spreader, to form a thicker coat. Alternatively, the spreader may be in the distal position throughout delivery, so that the fluid is distributed by it.

Finally, the spreader is retracted, and the light source is activated to deliver light to emission element 11 to polymerize the coating on the surface of the tissue. Optionally, further monomer solution can be delivered during the emission of light to build up additional thickness For this reason, both the delivery tube 22 and the main shaft 10 are preferably opaque to the light being used. This is conveniently achieved by constructing these elements of metal, such as standard syringe needle tubing. If the monomer solution is sensitive to room light, then the monomer syringe 48 should also be shielded or made of opaque material, and the monomer delivery path elements 21, 24 and 20 should likewise be opaque to the radiation wavelengths which initiate polymerization in the particular monomer/initiator combination. The rest of the device is made of any suitable material, such as a medical grade plastic. The device as a whole, or particular parts thereof such as the fluid dispensing pathway or the spreader, may be disposable.

In another embodiment, not illustrated, the elements 44, 55, 57 and 58 are omitted. The syringe plungers 41 are then exposed, and are driven directly by thumb pressure.

In an alternative embodiment, an additional trigger may be provided to connect to means for delivering a controlled amount of fluid with each squeeze of the trigger. Suitable ratchet means are known in the art; one such means is disclosed in co-pending application U.S. Ser. No. 08/036,128. In an alternative embodiment, separate fluid pathways may be provided for each of the two fluids. The separate pathways may be parallel or concentric. In the former case, separate spreading elements may be provided for each pathway.

Figure 2:
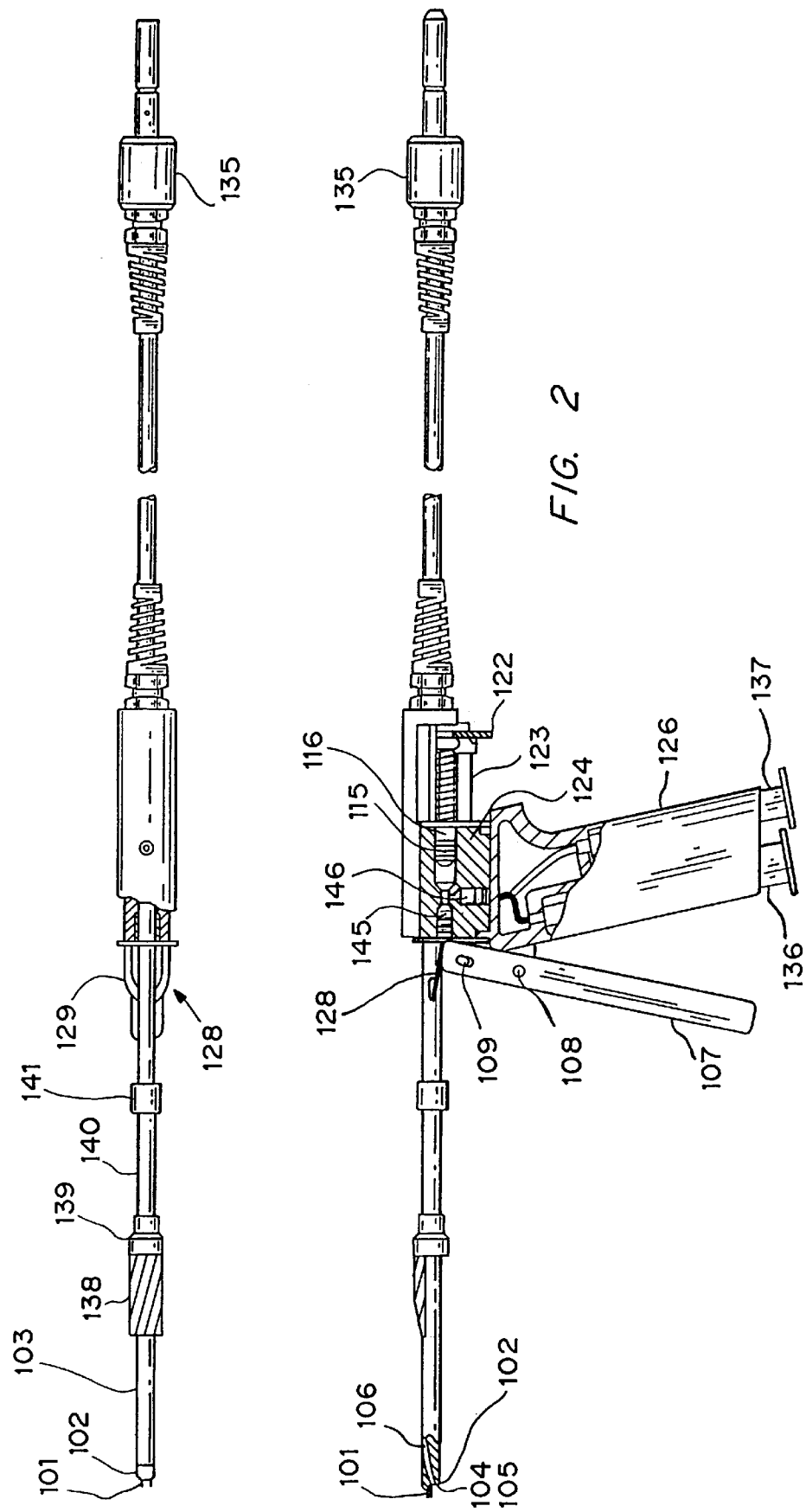
FIG. 2 is a schematic drawing of an alternate embodiment of a delivery device.

An embodiment of a delivery device incorporating both of these features is shown in FIG. 2. The device operates similarly to the device in FIG. 1, but uses a pumping mechanism composed of two pairs of one-way check valves, of which one pair is shown as 145 and 146, to pull fluid for delivery out of disposable syringes 136, 137, mounted in the handle 126, and inject the fluid through tubing 128, 129 into parallel delivery ducts terminating at orifices 101. The pumping action is driven by a trigger 107 mounted on a pivot 108. The trigger is linked via a connecting dowel 109 and a push rod 123 to either of a pair of spring 118-loaded pistons 116 by a switchable plate 122, similar in operation to that shown in FIG. 1, which couples to either of the pistons. The pistons are mounted in a housing 124 and sealed with O-rings 115. For illumination, an optical fiber 106 emitting through a window 104 with a diffuser 105, is connected through the body of the device to an optical connector 135 which delivers light from a remote source. The orifices, window and diffuser are carried in an end cap 102. Other features illustrated are similar to the device of FIG. 1, and include a main shaft 103), brush 138, and sliding brush shaft 140 with handle 141, to which the brush is removably attached with shrink-wrap 139.

Advantages of the device of FIG. 2 are the ability to deliver a known volume with each stroke of the trigger, and ease of changing syringes 136, 137 for replenishing reagent supply if required. As illustrated, one of the fluid delivery paths 128 is constructed from black flexible tubing, to avoid exposure of reactive monomer to light before delivery.

Figure 4:
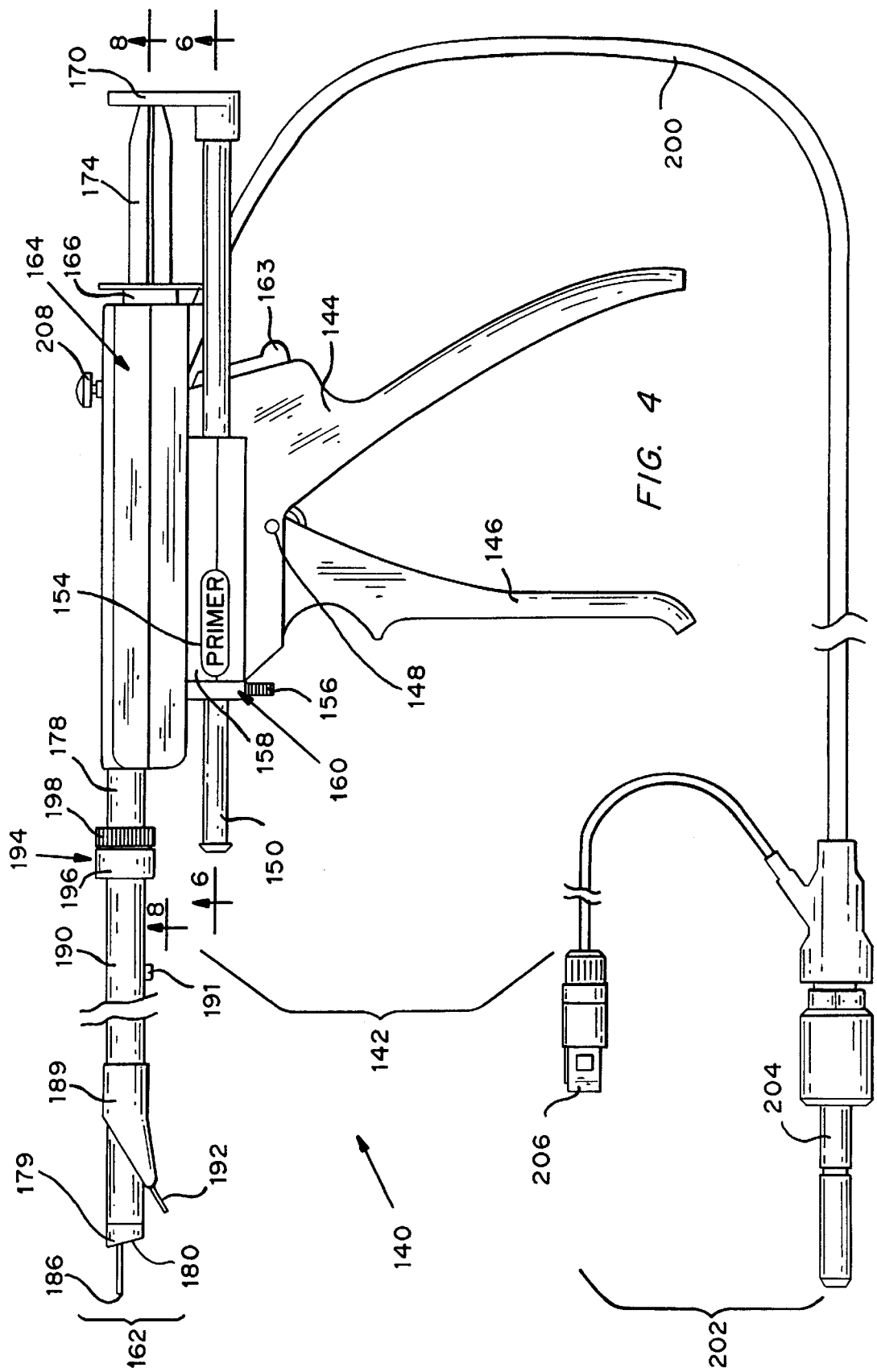
FIG. 4 is a schematic drawing of a dispenser according to another embodiment.

Another embodiment of apparatus for conducting primed photopolymerization, device 140, is illustrated in FIG. 4.

Device 140 is similar to devices described above and illustrated in FIGS. 1*a*–2 in that it includes a proximal portion adapted to be held by the hand of an operator of the device, a distal portion including an apertures for dispensing fluid at a treatment site, and a conduit arranged to connect a source of fluid to the aperture at the distal portion. More than one aperture and conduit are provided according to preferred embodiments, and device 140 is designed to allow particularly effective dispensing, independently or together, of at least two fluids to a target area via simple, one-hand operation of a right-handed or left-handed operator.

Device 140 includes a handle assembly 142 including a rear handle assembly 144 and a front handle, or trigger, 146 mounted so as to pivot about a pin 148 that passes through outer walls of rear handle assembly 144. Rear handle assembly 144 extends upwardly to define a cavity including (as described more fully below with reference to FIGS. 5 and 6), a set of recesses in which a set of lead racks 150 and 152 for driving plunger drivers are carried (lead rack 152 is hidden in FIG. 4), a ratchet mechanism arranged to drive lead racks 150 and 152, a switching mechanism arranged to operably connect trigger 146 with either of the lead racks, and a set of sleeves including displays 154 and 155 (hidden) that visually indicate the setting of the switching mechanism, that is, that indicate which of lead racks 150 or 154 are operably connected to trigger 146. A thumb wheel 156 is rotatable between first and second, detented positions, respectively, in which trigger 146 is operably connected to lead rack 150 or lead rack 152, respectively. A housing arrangement including a top cover 158 and a front cover 160 houses the ratchet mechanism, lead rack recesses, and portions of the sleeves carrying the displays. Front cover 160 houses gears that define, in part, the switching mechanism. The device is assembled with standard fasteners.

An upper, removable assembly 162 is removably connected to handle assembly 142 via sliding engagement locked by a latch 163 (described more fully below). Upper assembly 162 includes a syringe housing unit 164 including one or more recesses designed to carry one or more syringes. Preferably, two syringes (syringe 166 only is shown in FIG. 4) are mounted in recesses of the syringe housing unit during use. Plunger drivers 170 and 172 (172 is hidden) fastened to, or integral with the proximal ends of lead racks 150 and 152, respectively, can clamp syringe plungers 174 and 176, respectively, thereby operably connecting trigger 146 with either of the plungers.

Upper assembly 162 includes a main shaft 178 extending distally from the distal end of syringe housing unit 164. As in the embodiments illustrated in FIGS. 1*a*–2 and described above, central shaft 178 includes, at its distal end, an electromagnetic emission element 180 and one or more applicator tips, or outlets, for application of delivering fluid to a target area. In the embodiment illustrated, two applicator tips 186 and 188 (188 is hidden) are in fluid communication with syringes in unit 164 via conduits (hidden) extending from syringe recesses in syringe housing unit 164 through shaft 178. According to one embodiment, main shaft 178 and the applicator tips are made of stainless steel. According to another embodiment, the shaft and one or both applicators are made of a more flexible material. For example, in some settings it could be safer in terms of avoiding accidental puncture or other damage to tissue to fabricate the applicators of a flexible material such as medical grade plastic. According to another embodiment, main shaft 178 (and components therein, to the extent needed to achieve flexibility) is made of a flexible material and is an articulating shaft which can be steerable. The shaft is bendable and rotatable according to this embodiment.

A brush shaft 190 is coaxial with, and mounted on, main shaft 178 and is slidable proximally and distally thereon. Brush shaft 190 includes, on a ferrule 189 at its distal end, a spreading device 192 that can be a brush, pad, or the like, as described above with reference to FIG. 1a. As illustrated, spreading device 192 is a brush that is positioned to depend distally and downwardly from the distal end of brush shaft 190 at an exemplary angle of approximately 30 degrees. Spreading device 192 can be arranged to project axially, directly downwardly, or can be arranged in any other manner. Brush shaft 190 can be moved proximately over shaft 178 and spreading member 192 thereby positioned proximate the distal end 179 of main shaft 190, or moved distally thereby positioning the spreading member at a deployed position, preferably distally of distal end 179 of shaft 178. Limits on travel of brush shaft 190 proximally and distally on shaft 178, and rotational orientation of the brush shaft relative to the shaft, can be controlled by a pin 191 extending from the shaft 178 through a longitudinal slot (not shown) in brush shaft 190 within which the pin travels when brush shaft 190 is moved longitudinally relative to shaft 178.

A grip mechanism 194 is designed to allow, at one setting, brush shaft 190 to slide easily longitudinally on shaft 178 and to impede, at another setting, movement of the brush shaft relative to the shaft. Mechanism 194 includes a fixed portion 196 secured to or integral with brush shaft 190 and a rotatable portion 198 that threadingly engages fixed portion 196. An expandable element such as an o-ring (hidden) resides between portions 196 and 198 and, when portion 198 is screwed toward portion 196, the expandable element is squeezed and expands against the outer surface of shaft 178, frictionally engaging the shaft.

According to another embodiment (not illustrated), spreading member 192 can be mounted within a sleeve that surrounds shaft 178 and, when urged distally or when the surrounding sleeve is urged proximally, is exposed. In such an arrangement, the spreading member can spring outwardly when exposed and, and, when the member is in its retracted position, the shaft construction can be passed through a passage such as a trocar cannula.

According to a preferred embodiment, electromagnetic radiation emitter 180 is an emitter of light and is defined by a window, such as a sapphire window, optically coupled, via an optical fiber passing through shaft 178, syringe housing unit 164, and a flexible cable 200 to a source of light remote from device 140. Cable 200 can terminate in a set of connecters 202 including an optical coupler 204 connectable to a source of light such as a laser, and an electrical coupler 206. Electrical coupler 206 is connectable to an electrical source, and is electrically connected, via wiring in cable 200, to an electro-optical switch mounted in syringe housing unit 164. Electro-optical switches are known, and in accordance with the invention can be a simple on-off switch, a timed switch that when activated will cause illumination for a predetermined period of time such as 20 seconds, and the like. When connecters 202 are coupled appropriately to sources of light and electricity, when button 208 is pressed light exits emitter 180 at the distal end of shaft 178. When the button is not pressed, emitter 180 is blocked from receiving radiation. Such switches and optical and electrical connections are known.

Figure 5:
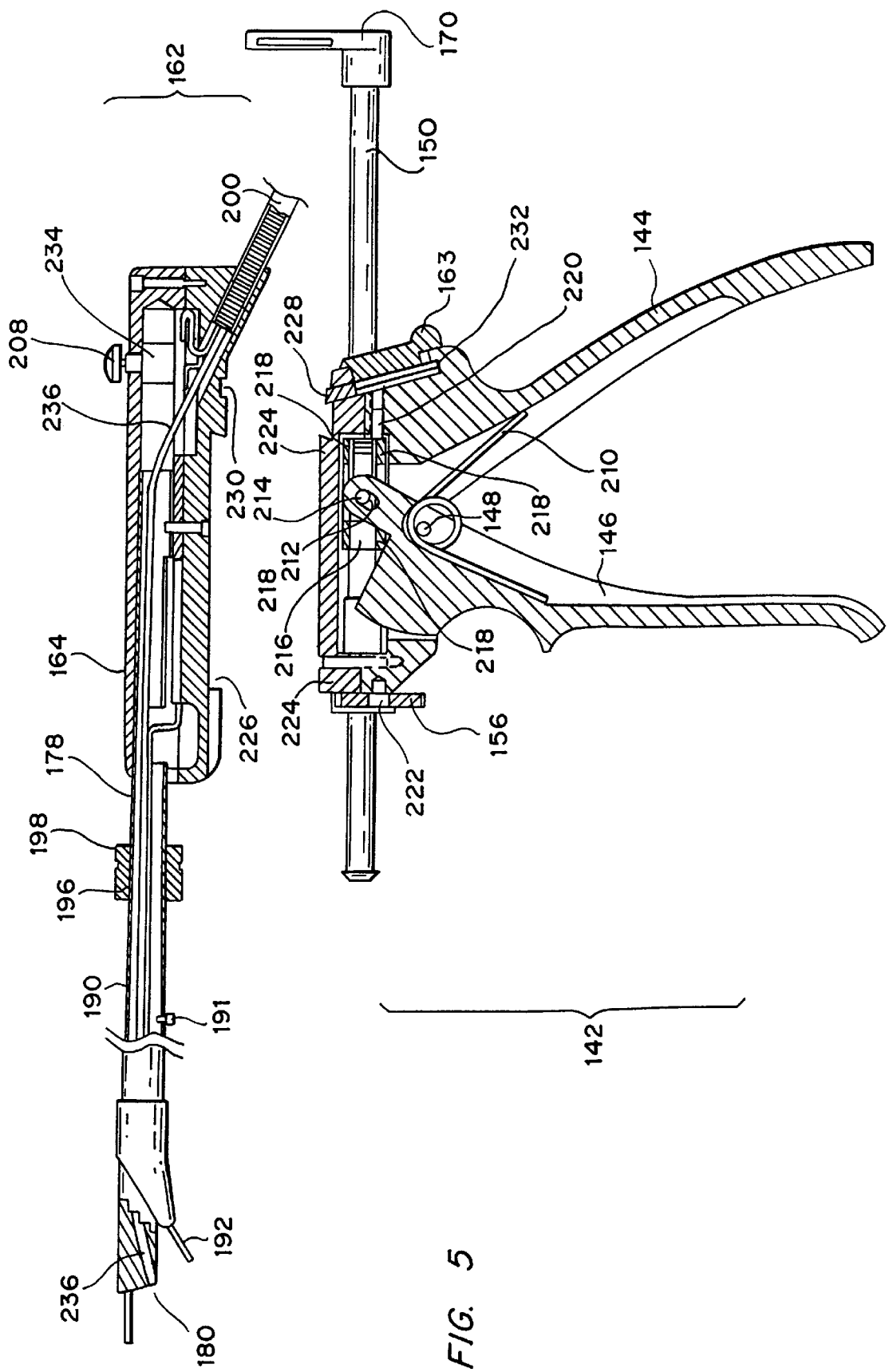
FIG. 5 is a cross-sectional view of the dispenser illustrated in FIG. 4 with the upper assembly detached.

Referring to FIG. 5, handle assembly 142 and upper assembly 162 are shown disconnected from each other in partial cross section. Upper assembly 162 can be fastened to lower, handle assembly 142 by engagement of a beveled protrusion 224, typically referred to as a dovetail, within a corresponding slot 226 in upper assembly 162. Upper assembly 162 is positioned atop the handle assembly, with the front of slot 226 aligned with the rear of protrusion 224, and moved forward until the rear of protrusion 224 abuts the rear of slot 226, whereupon protrusion 228 of latch 163 mates with indentation 230 of upper assembly 162. Latch 163 is urged upwardly by a spring 232, and can be moved downwardly easily by the thumb of an operator, allowing upper assembly 162 to be slid rearwardly and removed from handle assembly 142.

The upper and lower assemblies can be detached for a variety of reasons. According to one embodiment, the upper assembly is packaged as a sterile, one-use, disposable unit. The upper assembly can include, for example, a first syringe containing a photoinitiator and a second syringe containing a drug admixed with a monomer. The lower assembly can be reusable, or can be a limited-use unit, and used several or many times with various disposable upper assemblies. More than one upper assembly can be used in a single medical procedure where it is desirable to provide different combinations of formulations for slightly different therapies. Or, a procedure can be initiated where it will not be known until well into the procedure precisely which of several optional formulations will be most desirable, and clinical staff can have on hand a lower assembly and a plurality of upper assemblies each loaded with a different combination of agents.

Trigger 146 pivots about pin 148 and is urged forward, in its resting position, by spring 210 which also engages the rear handle assembly. When the trigger pivots rearwardly on pin 148 an upper portion of the trigger above the pin pivots forward. The upper trigger portion includes a slot 212 engaged by a clevis pin 214. Clevis pin 214 is connected to a bracket 216 which is connected to a ratchet carriage 218 housing a ratchet mechanism (described below), and the trigger is thereby operably linked to the rachet mechanism. An adjustable screw 220 limits rearward travel of ratchet carriage 218. A pin 222, about which thumb wheel 156 rotates, inserts into the front portion of the rear handle assembly. Upper, removable assembly 162 includes an electro-optical switch 234 controlling passage of light via an optic fiber 236 which passes from within cable 200, through shaft 178, to optical emitter 180, and is actuated by button 208 as described above.

Figure 6:
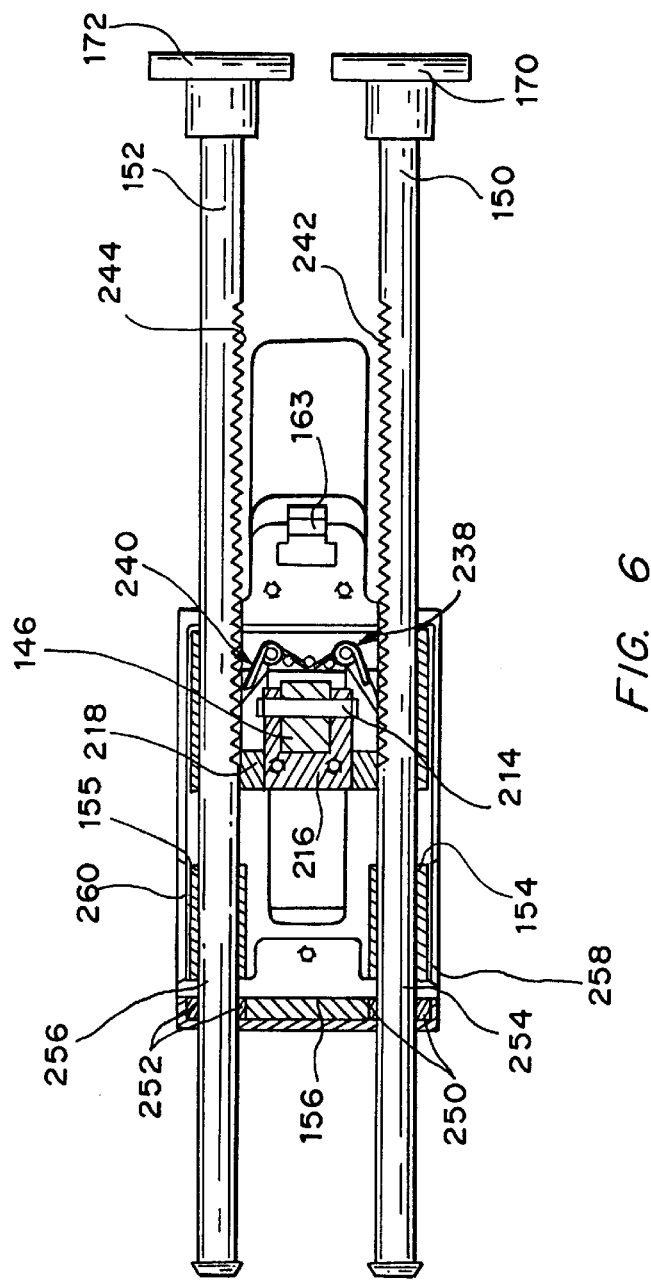
FIG. 6 is a cross-sectional view through section 6—6 of FIG. 4.

Referring now to FIG. 6, a ratchet mechanism for controlling application of fluid from syringes mounted in the syringe housing unit 164 is illustrated in greater detail. The ratchet mechanism is designed to operate by allowing pawls 238 and 240, respectively, to engage ratchet teeth 242 or 244 of lead rack 150 or 152, respectively, so that when trigger 146 is squeezed, one of plunger drivers 170 or 172 move forward to drive one of the syringe plungers. The arrangement can be adapted, as will be recognized by those of ordinary skill in the art, so that both of pawls 238 and 240 simultaneously engage teeth 242 and 244.

Figure 7:
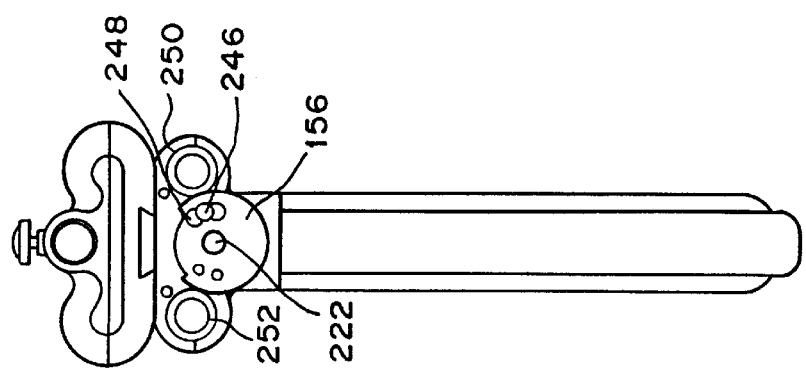
FIG. 7 is a front view of the device illustrated in FIG. 4.

With reference to FIG. 7 in conjunction with FIG. 6, operation of the ratchet mechanism will be described. Thumb wheel 156 is rotated on pin 222 between first and second positions defined by limits of the travel of a fixed pin 246 in a slot 248 of defined arcuate dimension. A detent mechanism (not shown) is positioned within handle assembly 144 and engages thumb wheel 156 at each of the two positions. Thumb wheel 156 includes teeth at its perimeter that mesh with teeth of drive gears 250 and 252. Drive gears 250 and 252 are secured to or integral with sleeves 254 and 256, respectively, which surround lead racks 150 and 152, respectively, from the drive gears rearward (proximally) to a point just past pawls 238 and 240. Each of the sleeves 254 and 256 includes an opening, or window aligned longitudinally with adjacent pawl 238 or 240, respectively. Each opening is positioned radially, and has an arcuate dimension such that, when the thumb wheel is in one position the slot is oriented so as to expose the teeth to the pawl, and when the thumb wheel is moved to the other position the slot is rotated away from the pawl and the sleeve blocks the pawl from engagement with the teeth. For example, when thumb wheel 156 is rotated clockwise (as viewed from the front as in FIG. 7) to the limit allowed by arcuate slot 248, sleeve 254 is rotated by drive gear 250 to a position in which the window in sleeve 254 exposes pawl 238 to ratchet teeth 242 of lead rack 150, while sleeve 256 is rotated by drive gear 252 to a position in which the window in sleeve 256 rotates away from pawl 240, and sleeve 256 blocks pawl 240 from engagement with teeth 244 of lead rack 152. In this position, when trigger 146 is squeezed and pivots on pin 148, it drives bracket 216 forward via clevis pin 214, which drives ratchet carriage 218 forward, which causes pawl 238 to engage teeth 242 and thereby to drive lead rack 150 and plunger driver 170 forward. Plunger driver 172 is not driven forward. When thumb wheel 156 is rotated counterclockwise to its limit and the trigger squeezed, the opposite occurs, namely, plunger driver 172 is driven forward and plunger driver 170 is not. Other arrangements for operably linking the thumb wheel (or other switch) to the sleeves would be apparent to those of ordinary skill, and can be constructed in accordance with the invention.

Sleeves 254 and 256 can carry displays 154 and 155, respectively, that are visible through windows 258 and 260, on respective sides of the top cover 158 of the handle assembly 142. The displays can be coordinated to rotate in and out of the windows so that, depending upon the position of thumb wheel 156, and which of the lead racks is engagable by the ratchet mechanism, indication is visibly made as to which syringe is operably linked to the active lead rack, that is, which component will be dispensed upon movement of trigger 146.

Each of lead racks 150 and 152 is rotatable about its axis into a first orientation in which its plunger driver 170 or 172, respectively, is orientated to engage the plunger of a syringe carried by syringe housing unit 164 and its teeth, 242 or 244, respectively, are positioned to engage pawl 238 or 240, respectively, and into a different orientation in which its plunger driver is in a position of disengagement from a syringe plunger and its teeth are rotated out of engagement with the adjacent pawl. As illustrated in FIG. 6, both lead racks are positioned to engage a syringe plunger and be engaged by a pawl.

Figure 8:
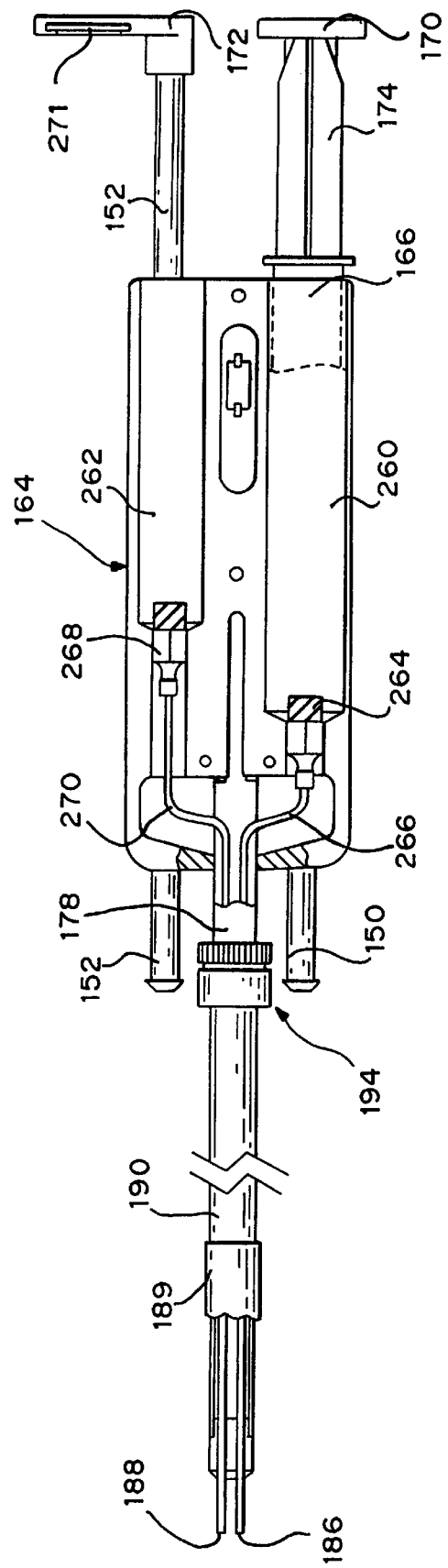
FIG. 8 is a partial cross-sectional view through line B—B of FIG. 4.

FIG. 8 is a partial cross section of upper, removable assembly 162, with a proximal portion only of syringe 174 illustrated. Syringe housing unit 164 includes individual syringe housings 260 and 262 each including a rearward-facing opening into which a syringe can be inserted. The syringe housings are of different sizes, as illustrated, but can be of the same size. Housing 260 includes, at its distal end, a fluid-tight connection such as a Luer-lock™ fitting 264 engagable by the distal end of syringe 174. Fitting 264 is connected to a conduit 266 which extends through main shaft 178 and terminates in applicator tip 186. Housing 262 includes also a Luer-lock™ fitting 268 connected to a conduit 270 extending through main shaft 178 and terminating in applicator tip 188.

As illustrated, lead rack 152 is positioned rotationally such that plunger driver 172 is not aligned with housing 262. In this position a syringe can be removed from, or inserted into, syringe housing 262. Additionally, in this position teeth 244 do not engage pawl 240 regardless of the position of thumb wheel 156, thus lead rack 152 can freely be moved forward or rearward to align plunger driver with the proximal end of a syringe in housing 262. Plunger driver 172 includes a recess 271 into which the proximal end of a syringe plunger fits snugly when the lead rack is rotated and the recess of the driver is moved laterally over the plunger end. Recess 272 is shaped so as not to allow a syringe plunger to escape proximally. That is, the plunger driver can be removed from the plunger only by rotating the lead rack and sliding the driver laterally away from the plunger.

Syringe 166 is positioned in syringe housing 260 (although the proximal end only of the syringe is shown) with lead rack 150 (hidden) positioned rotationally such that plunger driver 170 engages the proximal end of plunger 174. In this position, teeth 242 of lead rack 150 are oriented facing pawl 238 and, if thumb wheel 156 is rotated clockwise (with reference to the orientation of FIG. 7), when trigger 146 is squeezed teeth 242 are engaged by pawl 238, plunger driver 170 is driven distally, causing depression of plunger 174 into syringe 166 and delivery of the content of syringe 166 to applicator tip 186. As can be seen, when syringes are mounted in both syringe housings 260 and 262, Thumb wheel 156 can be rotated from a first, clockwise position in which actuation of trigger 146 causes the content of a syringe in housing 260 to be delivered to applicator tip 186, and a second, counterclockwise position in which trigger actuation delivers the content of a syringe in housing 262 to applicator tip 188.

Device 140 can be constructed according to several embodiments not illustrated. According to one, optic fiber-supplying cable 200 is connected to handle assembly 144, rather than to syringe housing 164, and when upper assembly 162 is coupled to lower assembly 142, an optical connection is made between the assemblies so as to connect emitter 186 to the light source. According to other embodiments, thumb wheel is located just above rear handle 144, and light button 208 is replaced with an auxiliary trigger in front of trigger 146 for alternate access. These and other modifications can be made. The device is fabricated from standard medical grade steel and/or plastic.

Referring now to FIG. 9, a hand held arrangement for delivery of material for primed photopolymerization, or other material is illustrated in cross section. A housing component 272 includes a syringe housing 274 for receiving a syringe 276. Housing 274 includes, at its distal end, a Luer-lock™ fixture 277 fluidly connected via a conduit 278 to a distal tip 280. Syringe 276 can be placed in housing 274 and secured thereto via Luer-lock™ fixture 277, and when plunger 282 of the syringe is depressed, the content of the syringe is delivered through distal delivery tip 280. Alternatively, the housing component 272 can be fitted with a distal applicator 284 including a cavity 286 into which a distal portion 288 of housing component 272 fits frictionally via, for example, a standard Luer™ type fitting. Cavity 286 is fluidly connected, via conduit 290, to a distal tip 292 located, as illustrated, within a brush 294. This extends the delivery pathway distally, and provides a brush as a spreading element. The spreading brush can be replaced with a variety of devices such as pad, etc., as described above.

FIG. 10 illustrates an assembly 296 defined by the assembled components syringe 276, housing component 272 and extender 284 including brush 294.

According to another embodiment, syringe 276 is coupled directly to extender 284 carrying brush 294, without housing component 272. Applicator component 284 includes, at its proximal end, a Luer-lock™ fitting 298 that can be coupled to the distal end of syringe 276. Thus, a relatively longer device as illustrated in FIG. 10 and including syringe housing 274, or a relatively shorter device defined by applicator 284 coupled directly to syringe 276, can be assembled.

Figure 11:
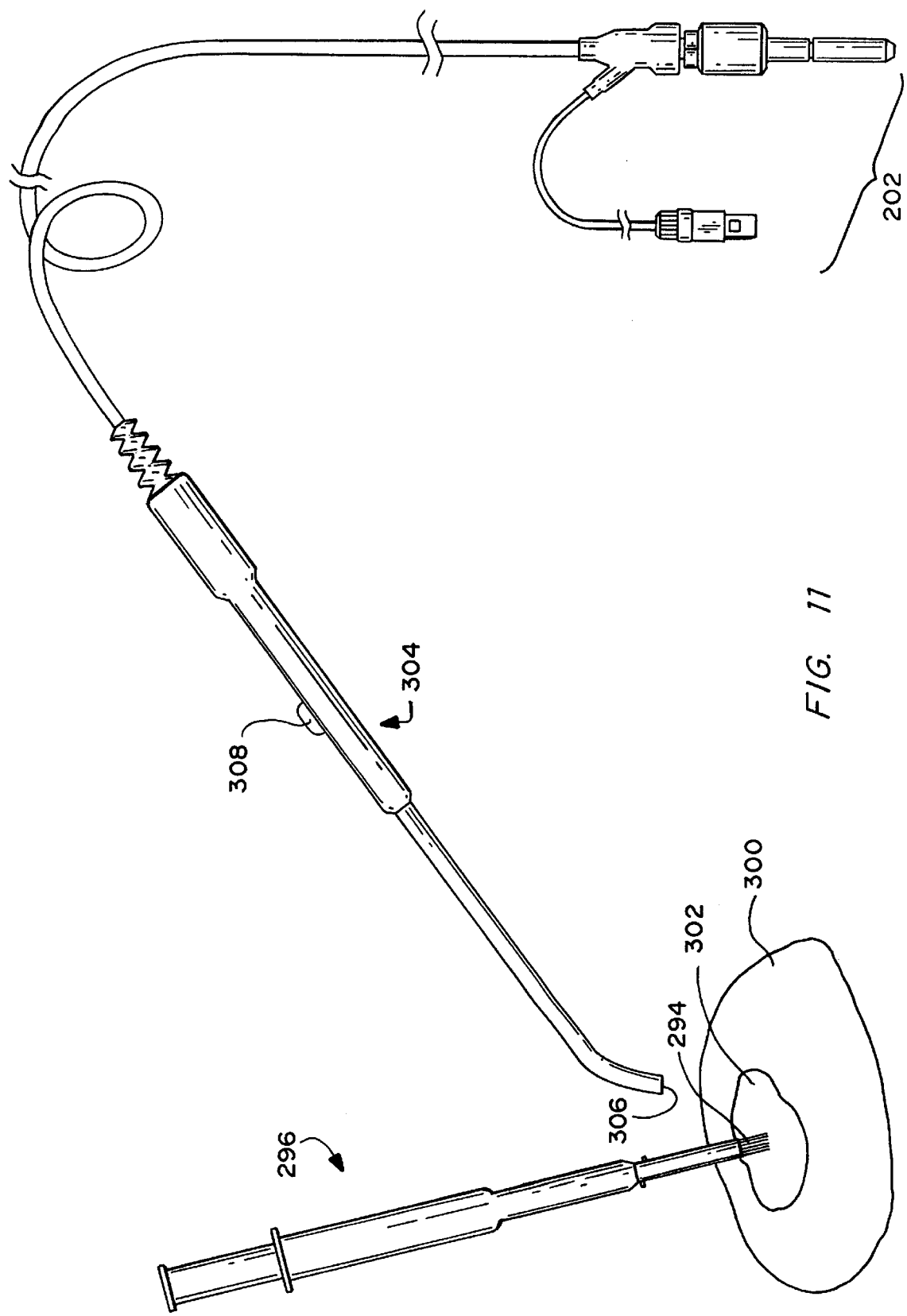
FIG. 11 illustrates schematically the use of the device illustrated in FIG. 10 in conjunction with a light wand.

Referring now to FIG. 11, a schematic illustration of use of the device illustrated in FIG. 10 is presented. As illustrated, device 296 is used to apply to a surface 300 a photopolymerizable material such a monomer/initiator formulation 302. After application of material 302 to surface 300 (via dripping from the applicator tip 292 or introduction of the material within brush 294 followed by direct transfer to surface 300 from the brush), material 302 can be spread or positioned accordingly by brush 294. Then, a radiation or light wand 304 having a distal, light-emitting end 306 can be brought into position and actuated via depression of an electro-optic switch 308, whereupon photopolymerizable material 302 is polymerized or crosslinked, optionally hardened. Wand 304 is connected to optical end electrical couplings 202.

In all embodiments of devices for application of material, any component described herein, in any formulation or combination, or any other component known to those of skill in the art can be delivered via the device Preferably, the device is loaded with an initiator, monomer, drug, co-initiator, co-monomer, surfactant, stabilizer, and/or plasticizer as described herein, but it is to be understood that the devices of the invention can be used with other compositions. Of course, according to preferred embodiments components of the invention are sterile or sterilizable, that is, able to be readily sterilized and adapted to be used in a medical setting.

PACKAGING

The materials for making the coating can be packaged in any convenient way, and may form a kit, alone or together with the application device. The reactive monomers are preferably stored separately from the initiator, unless they are co-lyophilized and stored in the dark, or otherwise maintained unreactive. A convenient way to package the materials is in three vials (or prefilled syringes), one of which contains concentrated initiator for priming, the second of which contains reconstitution fluid, and the third containing dry or lyophilized monomer. Dilute initiator is in the reconstitution fluid; stabilizers are in the monomer vial; and other ingredients may be in either vial, depending on chemical compatibility. If a drug is to be delivered in the coating, it may be in any of the vials, or in a separate container, depending on its stability and storage requirements.

It is also possible, for a more "manual" system, to package some or all of the chemical ingredients in pressurized spray cans for rapid delivery. If the monomer is of low enough viscosity, it can be delivered by this route. A kit might then contain a spray can of initiator; a spray can or dropper bottle of monomer, initiator and other ingredients; and an optional spreading or rubbing device. If the monomer and initiator system are designed to polymerize under the influence of natural or operating room light, possibly with the supplement of a chemical initiator or carrier such as a peroxygen compound, then the technique could be suitable for field hospital or veterinary situations.

EXAMPLES

EXAMPLE 1

Relative adhesion of coating to primed and unprimed surfaces.

Fresh pig lung was primed in one area with a solution of photoinitiator (Eosin Y, 1 mg/mL (1000 ppm) in normal saline) and in another area with normal saline (prior art control). Excess fluid was removed by blotting. About 0.5 mL of monomer solution was applied to each spot. The monomer was polyethylene glycol (35,000 Daltons) terminated with caprolactone (average of 3.3 caprolactone groups per polyethylene glycol molecule) and capped with acrylic acid, essentially as described in Hubbell et al. The monomer solution contained 15% monomer (w/w), 90 mM triethanolamine, 20 ppm (w/w) Eosir, and 5 microliters/mL vinylpyrrolidone (v/v). The samples were irradiated with green light until cured (40 sec. at 100 mW/cm$^2$) into a firms transparent gel. Initial adherence was seen in both primed and control spots, although the primed spots had better overall adherence.

The lung was connected to a pressure-controlled inflation apparatus, and subjected to chronic fatigue for 1 hour of pneumatic inflation pressures at 25 to 30 cm of water, in 6 second cycles. This was designed to simulate the effects of breathing. After the fatigue test, the primed gel spots were still adherent, but the control gel spots could easily be lifted from the lung surface with forceps. Thus, adhesion under chronic stress was better with priming before polymerization.

EXAMPLE 2

Sealing of wedge resection of lung.

In lung operations, it is common to make a "wedge resection" to remove diseased areas. A combination stapler/cutter is used to simultaneously cut and staple along one side of the wedge to be removed, and is then used to staple and cut the other side so that a wedge-shaped piece of lung is removed, while the remaining lung is simultaneously stapled closed. Despite a high staple density, the staple lines are prone to leak air, which can produce severe complications in a patient undergoing such an operation.

Frozen-thawed pig lungs were wedge-resectioned, using a ProxiMate™ TLC 55 reloadable linear cutter/stapler (Ethicon; Somerville, N.J.). Every second staple was omitted from the outer staple lines in the cassette to reliably induce leaks. Lungs were inflated with air to a pressure of 40 cm H$_2$O, and leaks were observed by pushing the stapled area just under the surface of a water bath (similar to leak testing of an inner tube). Next, staple lines were primed with 1000 ppm Eosin Y, blotted, and treated with the macromer mixture of example 1 which was then cured as described.

In a standard test for durability, the lungs were inflated to 20 cm water pressure for 10 cycles, over a period of 1 minute, and then held for 30 seconds at 40 cm water. The primed and sealed lung sections showed no leaks, demonstrating the effectiveness of the priming system in sealing known leaks.

Finally, pressure was increased in the primed lungs to determine the maximum pressure before leakage. Small leaks were typically seen at 75 cm water or above.

EXAMPLE 3

Lap/Shear Strength of Primed and Unprimed Bonds.

Adhesion under shear of gel to rat skin was determined on an Instron™ apparatus using standard methods. The biological surface was rat back skin, freshly removed from euthanized animals. It was glued to a glass slide, and treated as described below. A casting chamber was positioned above the skin, which also contained a gauze mesh which protruded from the chamber. Monomer solution was injected into the chamber and polymerized. The chamber was removed, and the tensile strength of the bond was determined by shearing the lap between the glass slide and the gauze mesh in a standard load cell on the Instron.

Skin treatments included none (control); primed; primed and pre-coated with monomer solution by drip; and primed, pre-coated with monomer solution by drip, and rubbed or mixed with a brush. A monomer solution as in Example 1 was applied, except that the monomer, "8KL5", had a smaller PEG molecule (8000 D), and was extended with lactate groups rather than caprolactone groups. With unprimed skin, a different initiator, Irgacure™ 651 (Ciba Geigy), was also used in the gelling monomer mixture.

With the non-primed Irgacure® system, average load at failure for 6 to 8 samples ranged from 49 grams of force with low-intensity mixing of monomer onto the surface, to 84 to 274 g. with rubbing. Similar results were obtained with the Eosin catalysed system with no primer (146 g average, range 80–220). When the tissue was pre-primed with Eosin, and monomer solution was thoroughly mixed with a brush, the failure force increased to 325 g (range 220–420). Thus priming can quantitatively improve early adherence, in addition to its much larger improvement in adherence after flexing.

EXAMPLE 4

Sealing of a bronchus.

A bronchus was stapled and cut during lobectomy by the techniques described for wedge resectioning. The staple line was coated as described in example 2, likewise preventing or stopping air leaks.

EXAMPLE 5

Sealing of a laceration.

A laceration 2 mm deep by 2 cm long was made on an isolated lung with a scalpel; the scalpel was taped to control the depth of cut. The lung was tested and found to leak. The laceration was primed, filled with monomer solution containing initiator, and the monomer was photopolymerized. The leak was sealed by this procedure.

EXAMPLE 6

Coating of a medical device.

A length of polyurethane tubing extrusion used for catheter shafts was dipped into an aqueous solution containing 20 ppm eosin. Excess eosin was rinsed off with water. The primed tubing was dipped into a solution containing 10% monomer (type 8KL5, as in example 3), 90 mM triethanolamine, 5 ppm vinylpyrrolidone, and 20 ppm eosin. Excess monomer was allowed to drip off. The monomer layer on the tubing was then photopolymerized to form an adherent gel coating. The adherence was strong enough to survive sectioning of the tubing with a razor blade; photomicrography showed complete adherence of the gel to the tubing. As a prior art control, the shaft was not primed. After dipping the un-primed shaft into the same monomer solution, the coating on the shaft was photopolymerized. A gel was formed, but failed to adhere to the shaft, and fell off during handling.

EXAMPLE 7

Priming for surface adherence

Two surfaces of Pebax™ polyeteramid were stained with 1000 ppm Eosin Y and rinsed. Polymerizable monomer solution (10% 8KL5 in water containing 20 ppm eosin) was placed between the surfaces, and the sandwich was exposed to green light. Gel formed in the interface and held the surfaces together. In a control experiment, in which the surfaces were not primed, polymerization of the monomer occurred but no significant adherence of the surfaces was found.

EXAMPLE 8

Priming of surfaces.

On exposure to 1000 ppm of Eosin Y, surfaces of Teflon™ fluoropolymer and of polyethylene were observed to stain significantly. When monomer was added to such surfaces, and allowed to stand briefly, gels were formed on illumination. Adherence seemed inferior to that obtained on polyurethane.

EXAMPLE 9

Priming of Uterine Horn and Adherence of Gel Layers.

A model system was established for placing of barriers on mammalian uteruses after operations. Freshly excised uterine horns from euthanized pigs were removed from a saline bath and treated with 1000 ppm Eosin. Controls were not primed. Polymerizable monomer solution as in Example 7 was applied to the primed and control areas. Adherence of gel layers to the primed areas was very firm, while gels on control areas could be dislodged.

EXAMPLE 10

Water-sensitive initiation.

It is known to use tributylborane as a water-sensitive initiator of bulk polymerization. In this example, it is shown that TBB can serve as an initiator in interfacial polymerization, and thus as a primer in the present invention.

1 M tributylborane (TBB) solution in THF was purchased from Aldrich. Lyophilized 35KL4A2 reactive monomer containing triethanol amine and eosin was made in these laboratories. Polyethylene glycol 400 (PEG 400) was obtained from Union Carbide). Of the lyophilized powder of 35KL4A2, 0.5 gram was dissolved in 9.5 grams of PEG 400. The mixture was warmed using a heat gun up to 40–50° C. to facilitate dissolution. To this solution, 30 µL of vinyl pyrrolidinone were added as a comonomer.

Using a glass syringe, 2 ml TBB solution were transferred to a sprayer, of the type used with thin layer chromatography plates. A small amount of TBB solution was sprayed on a glass coverslip and the PEG 400 solution containing 35KL4A2 was applied on the TBB solution. An immediate polymerization of the solution was noticed. The polymerized film was insoluble in water indicating crosslinking.

Similar polymerization was carried out on pig lung tissue. A small amount of TBB solution was sprayed on approximately 3 cm$^2$ of lung tissue. A 35KL4A2 solution in PEG was applied on top of the TBB solution. A small amount of TBB solution was also sprayed on top of the monomer solution. A well adherent film of 35KL4A2 on lung tissue was noticed. The polymerized film was elastic and well adherent to the tissue.

In an alternative procedure, application of the TBB initiator to tissue may be followed by application of monomer solution containing a photoinitiator, such as 20 ppm eosin. Photopolymerization is then used to build a thick layer of gel onto the initiated priming layer. Good adherence is predicted.

EXAMPLE 11

Combination of redox free radical initiation systems with photoinitiation and/or thermal free radical initiation systems for increased polymerization speed.

Previous visible light photopolymerization of Focal macromonomers uses the aqueous eosin Y/triethanolamine photoinitiation system. This reaction has been observed to generate peroxides when carried out in the presence of dissolved oxygen in the buffer. One may exploit these generated peroxides as an additional source of free radical initiators for polymerization using a Fenton-Haber-Weiss style reaction. In an effort to use these formed peroxides as polymerization initiators, ferrous ion in the form of ferrous sulfate was added to the eosin Y/triethanolamine buffer and used in the photopolymerization of Focal macromonomers. Using an indentation style hardness test, gel stiffness as a function of illumination time was used as a measure of gel cure.

In an experiment to evaluate the effectiveness of 50 ppm ferrous ion on the gelation of the Focal macromonomer 8KL5, two buffers were prepared. The first buffer was prepared in deionized (DI) water using 90.4 mM triethanolamine(TEOA) and pH adjusting to 7.4 with 6 N HCl. The second buffer was prepared similarly but with the addition of ferrous sulfate such that there would be approximately 50 ppm ferrous ion available. These buffers were used to prepare a 10% (w/v) 8KL5 gelling solution with 1 microliter of vinyl pyrrolidinone per ml of gelling solution added as a comonomer. These solutions were then divided into gelling samples and had 20 ppm of eosin Y added to them. These samples were then illuminated using an all lines Ar laser at a power of 100 mW/cm$^2$. All illumination timepoints were done in triplicate and kept dark until stiffness testing was performed. In comparing a 10%(w/v) Focal macromonomer gelling solution with and without 50 ppm of ferrous ion added, the gel with the added iron gave significantly more cured gels than did the gel without iron.

It is further believed that any free radical initiation system, especially aqueous ones, capable of generating soluble peroxides can be greatly enhanced by the addition of soluble metal ions capable of inducing the decomposition of the formed peroxides.

EXAMPLE 12

Redox-accelerated curing ("dual cure") of primed systems.

A redox-accelerated system was compared to a purely photoinitiated system for priming tissues. The accelerated system was found to be especially effective in the presence of blood, which attenuates the light used in photopolymerization. An acute rabbit lung model of sealing of air leaks was used. A thoracotomy was made under anesthesia in the intercostal space of the rabbit. Anesthesia was induced using an intramuscular injection of ketamine-acepromazine. The seventh rib was removed to facilitate access to the lungs, and the animal was maintained on assisted ventilation. A laceration, about 8 mm×2 mm, was made on each of the middle and lower lobes of the lung. Air and blood leaks were immediately apparent. Bleeding was tamponaded using a gauze sponge, and the site was then rinsed with saline. Some blood remained, and a slow ooze of blood and air leakage from the site was still persistent on ventilation.

Two formulations were compared. In the first formulation, the priming solution contained 500 ppm Eosin Y and 90 mM TEOA (triethanolamine) in WFI (water for injection), while the macromer solution contained 15% w/v macromer (type 35KL4), 20 ppm Eosin Y, 5 mg/ml vinylcaprolactam, and 90 mM TEOA in WFI.

The second formulation contained 500 ppm Eosin Y, 15% 35KL4, and 3 mg/ml ferrous gluconate in WFI in the primer, and the same macromer solution as in the first formulation, supplemented with 500 ppm t-butyl peroxide.

Application methods were the same for both formulations, and consisted of application of 1 ml primer with gentle brushing, followed by application of 0.5 ml macromer solution by brushing, and then illumination with blue-green light at 100 mW/(square centimeter) while dripping an additional 0.5 ml of macromer. Total illumination time was 40 sec. Gels were formed on the tissue by both treatments, and the air and blood leakages were sealed.

Acute adhesion of the gel to tissue was rated on a scale of 1 (poor) to 4 (excellent). The first formulation scored 1.5, and the second scored 3.5. A notable improvement in adherence of the gel to the living lungs was seen with the use of the dual cure system.

EXAMPLE 13

Optimization of iron concentrations.

The objective is to find a redox system which does not instantaneously gel the macromer, and which can also be cured by light. Various formulae were prepared, and their polymerization was studied.

A stock monomer solution (solution 1) contained 15% w/w "35KL4" macromer, lot 031395AL, in TEOA buffer (90 mM triethanolamine, neutralized to pH 7.4 with HCl, in water for injection), and 4000 ppm VC (vinylcaprolactam) and 20 ppm eosin Y (photoinitiator). The buffer was selected to be compatible with dissolved iron.

Iron-monomer solution (solution 2) contained in addition 20 mg/ml of ferrous gluconate, 5.8 mg/ml of fructose, and 18 mg/ml of sodium gluconate.

Peroxide primer (solution 3) contained: 500 ppm eosin in TEOA buffer, plus 5 microliter/ml of 10% tertiary butyl peroxide. An alternative priming solution (3b) contained in addition 10% 35KL4.

Serial dilutions of one volume of iron monomer with two volumes of stock monomer were made, and the gelation time, in the absence of high-intensity light, upon addition of 1 volume of priming solution (3) to two volumes of diluted iron monomer was determined. The stock iron monomer and the 1:3 dilution gelled very rapidly (1–2 seconds), and a 1:6 dilution gelled in 3–4 seconds. The 1:9 dilution gelled very slowly—no rapid gelation, and partial gelation after 1 hour. Further dilutions (1:27, 1:81) did not gel for at least one hour.

The formulation with 1:9 dilution, containing about 2.2 mg/ml of ferrous gluconate, was tested for its ability to adhere to excised tissue, and to gel in the presence of blood. Acute adherence was obtained with 1:9 iron monomer solution when primed with the basic peroxide priming solution, but better adherence was found with monomer-containing priming solution (3b).

In solution, a mixture of monomer solution (0.3 ml) and normal primer (0.13 ml; without peroxide), which polymerized when exposed to intense argon laser light, would not gel after addition of 2 drops of blood (about 33 mg). However, a mixture of the same volumes of 1:9 iron monomer, primer 3b, and blood gelled in 5 seconds on exposure to the same light source. Omission of the Na gluconate and fructose did not significantly change the gel time. The mixed formulation (iron monomer, peroxide primer, and blood) could be held for three hours in amber glass at room temperature with only slight decrease in the gelling time on exposure to light.

Thus, the formulation is sufficiently stable and controllable under operating room conditions, so that a preparation could be reconstituted at the start of the operation, and the material would be useful and applicable to tissue throughout the operation.

EXAMPLE 14

Adherence to tissue at varied concentrations of peroxide and iron.

Areas of excised fresh or frozen-thawed pig lung were primed with a photoinitiator, and a gel formed on the spot by dripping of photoinitiator-containing monomer, using the devices of FIG. 1 or of FIG. 2. In contrast to the previous example, the iron (ferrous gluconate) was in the primer, and the peroxide in the monomer solution. Gels formed by illumination at peroxide concentrations ranging from 76 to 900 ppm, and iron concentrations ranging from 1500 to 5000 ppm, had at least moderate adherence to tissue after overnight incubations.

EXAMPLE 15

Factorial Screening Experiment for Gel Adherence with respect to varying quantities of N-vinyl Pyrrolidone, macromonomer concentration and triethanolamine.

The purpose of this experiment was to examine the effects of varying amounts acrylic acid, n-vinyl pyrrolidone and triethanolamine in an effort to understand the interfacial polymerization process variables to get uniform adherent gel coating. The chemistry related variables which affect the photopolymerization and gel adherence qualities include Eosin concentration in tissue, monomer concentration, PEG diacrylate content, and acrylic acid. The factorial experimental design was to screen the statistical significance of the variables mentioned above, in terms of individual and interactive effects. Various combinations of acrylic acid, monomer concentration, triethanolamine and n-vinyl pyrrolidone were examined in terms of gel-tissue adherence as the response factor.

The experimental results of the factorial experiment outlined below were graded in accordance to the performance with respect to two tests:
(1) The first time point was the gel adherence at 2 hours, the grading being conducted on a scale of 1–5.
(2) The second time point was the gel adherence in response to low shear force on adherence at 24 hours, the grading being conducted on a scale of 1–5.
(3) Grading was conducted by a person who did not know the composition of the test materials.

Materials

Pig aorta tissue, cut into small sections. The aortic tissue should be preferably devoid of fatty deposits; CCD camera; dissecting materials; visible light source (514 nm); timer; scintillation counter and vials.

Procedure (1) As given in the factorial design, there were 16 experiments. 32 scintillation vials were marked in sets of duplicate, such as 1.1, 1.2, etc. Since there were 16 experiments, there were 32 vials in total.
(2) A stock solution of 10% acrylic acid was prepared in PBS. 2.50 $\mu$l of 10% acrylic acid was added to the vials that had 10 ppm of acrylic acid in the experimental design.
(3) Triethanolamine solution was prepared by measuring, by weight, 0.67 g triethanolamine: 400 ml of PBS. The solution was pH balanced to 7.4 by adjustment with 6N HCl solution.
(4) The required amounts of VP, triethanolamine, acrylic acid was mixed in 5 ml of PBS.
(5) The required amounts of macromonomer were mixed in, in accordance to the experiment. pH measurements was taken again, to ensure that the solutions were at pH 7.4.
(6) The pig aorta tissue was sectioned into small rectangular pieces. All sectioned pieces were chosen, such that the tissue surface was devoid of fatty deposits.
(7) 32 scintillation vials were prepared for the storage of the gelled tissue, by the placement of 5 mls of PBS solution in each one.
(8) A 1 mg/ml solution of Eosin in PBS was prepared.
(9) A piece of aortic tissue was placed flat upon a clean surface, and a swab dipped in the eosin solution was pressed upon a spot for exactly 10 sec. Another spot was prepared upon the tissue with the eosin dipped swab. The spotted tissue was rinsed in PBS. The tissue section was then grasped with sharp tweezers and placed in the rectangular 4-well glass slide chambers. The tissue should lie flat inside the chambers.
(10) 400 $\mu$l of the macromer solution were placed in the well, and the plate was placed exactly under the collimated beam of the fiber optic cable. The tissue was exposed for exactly 15 sec.
(11) The exposed tissue was grasped gently with tweezers and placed in the scintillation vial with 5 mls of PBS. The vials were placed inside the shaker for 2 hours to hydrate.
(12) After 2 hours, the gels were viewed through a microscope to view the gel adhering to the tissue. surface. The tissues were graded for adherence, quality and shape on a scale of 1–5. The microscope was fitted with a SONY CCD Camera. The physical state of the gel can be viewed satisfactorily for grading from 1–5.
(13) After the examination, the vials were placed in the shaker for approximately 24 hours, to examine the effect of low shear rate on the interfacial gel.
(14) The gels were examined for gel adherence and quality on a scale of 1–5.

TABLE 1

| | Experiments | | | |
|---|---|---|---|---|
| Rows | Monomer Conc. | TEA con. ($\mu$l of 60% soln) | VP ($\mu$l) | Acrylic Acid |
| 1 | 10 | 5 | 1 | 0 |
| 2 | 10 | 5 | 1 | 10 |
| 3 | 10 | 5 | 3 | 0 |
| 4 | 10 | 5 | 3 | 10 |
| 5 | 10 | 20 | 1 | 0 |
| 6 | 10 | 20 | 1 | 10 |
| 7 | 10 | 20 | 3 | 0 |
| 8 | 10 | 20 | 3 | 10 |
| 9 | 23 | 5 | 1 | 0 |
| 10 | 23 | 5 | 1 | 10 |
| 11 | 23 | 5 | 3 | 0 |
| 12 | 23 | 5 | 3 | 10 |
| 13 | 23 | 20 | 1 | 0 |
| 14 | 23 | 20 | 1 | 10 |
| 15 | 23 | 20 | 3 | 0 |
| 16 | 23 | 20 | 3 | 10 |

(15) The gels were graded according to the following scale:

TABLE 2

Gel Adherence Rating System

| GRADE | CRITERION |
|---|---|
| 1 | Intact |
| 2 | Some edges loosened but otherwise intact |
| 3 | 50% intact |
| 4 | gel only attached by some edges, otherwise not - adhered. |
| 5 | Not adhered |

Observations

Figure 3:
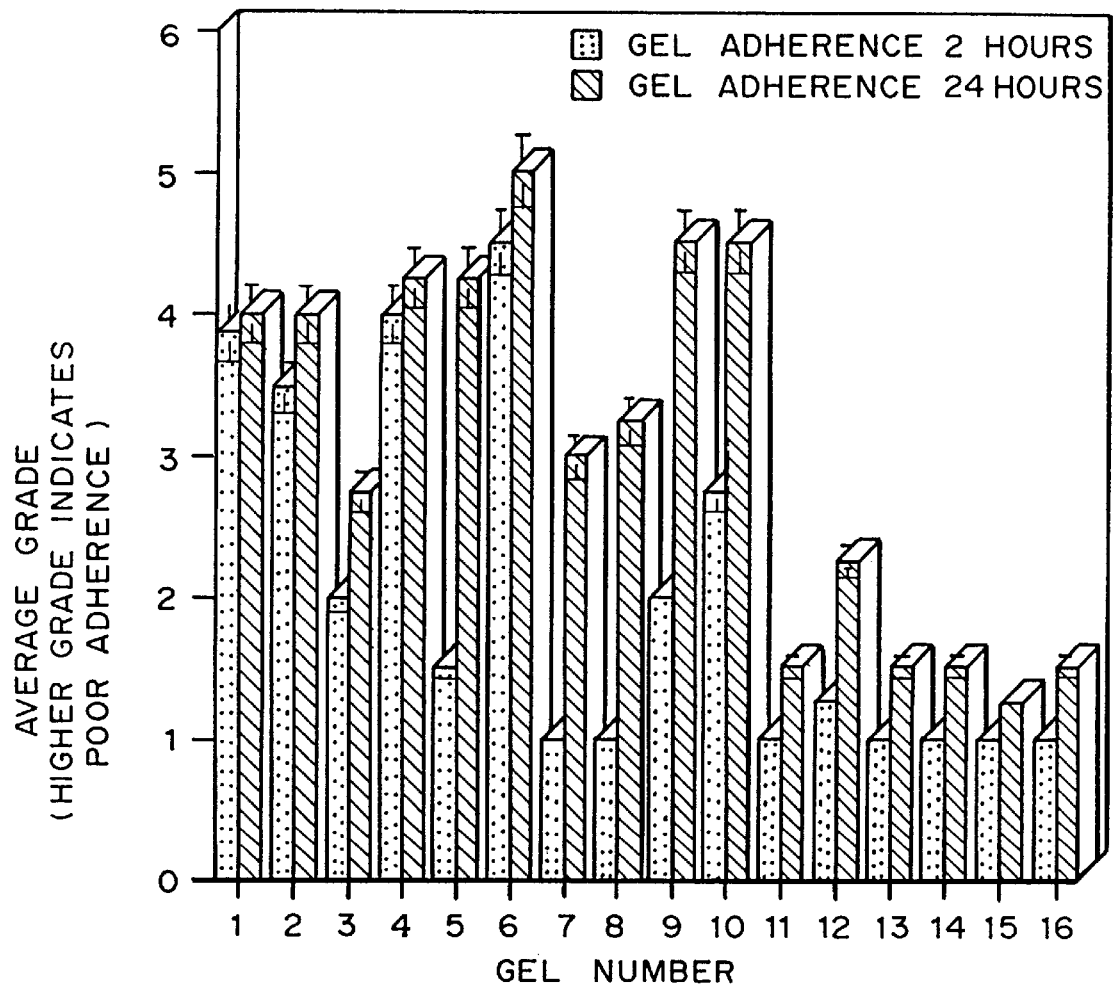
FIG. 3 is a graph of the relative adherence to tissue of several formulations, on a scale where a higher score indicates poorer adherence.

The adherence score is presented in FIG. 3, in which a higher score represents worse adherence, in contrast to previous examples.

A Factorial Statistical Analyses of the gel adherence scores with respect to the variables individually, and in interaction with the other variables (acrylic acid, triethanolamine, N-vinyl pyrrolidone, monomer concentration) was performed using a Statistical Modeling Package. P values closer to zero indicates the statistical significance (95% confidence interval). The p-values for all the variables and their interactive effects were determined.

It was found that the monomer concentration was the dominant influence and highly significant. The TEA concentration was also significant. Variation in VP and acrylate were not significant in these ranges.

EXAMPLE 16

Further tests of influence of monomer concentration and initiator on adherence of gels to tissues.

Variations in tissue adherence of gels can also be seen in non-primed systems. As noted in U.S. Pat. No. 5,410,016 to Hubbell et al, , and in Dumanian et al, *Plastic & Reconst. Surg.* 95(5), 901-07 (1995), tissue sealing and adherence may also be obtained without priming.

Adhesion strength was determined by testing the strength of a lap shear of gel, which was formed between a glass and a plastic slide. One slide was fixed; the other was connected by a string over a pulley, with a cup on the vertical end of the string. After formation of the gel, the cup was filled from a peristaltic pump, and the stress at which failure occurred was calculated from the weight of the partially-filled cup at failure.

As a standard, 150 microliters of a solution containing 23% monomer, type 8KL5, and 300 mg/ml of Irgacure™ initiator, was spread between the slides and polymerized. This produced a high level of adherence, as determined by force to failure. A low-adherence control was the same solution with 10% monomer.

The following variations did not improve adherence: coating each slide with 10 microliters of 10% monomer solution containing 3x or 10x the amount of initiator, followed by application of 140 microliters of 10% monomer and polymerization. Doubling the precoating to 20 microliters was also ineffective. However, precoating with 23% monomer, at normal initiator level, significantly improved overall adherence.

Further testing used bleeding in a cut liver as a test. In this situation, 23% monomer was much more effective than lot monomer in stopping bleeding. It appears from these experiments that higher monomer concentrations intrinsically adhere to tissue better than lower concentrations, at least in the ranges tested.

EXAMPLE 17

Redox interfacial primed system.

It was demonstrated that non-photopolymerization techniques can produce gels adherent to tissue. Thinly-sliced ham was soaked in deionized water, and a 1 by 2 inch piece was folded in half and the outer edges were bonded together. First, 0.1 ml of solution A was applied to the joint (Solution A contained 10% monomer 8KL5, 0.3% hydrogen peroxide, and 0.3% NVMA (N-vinyl N-methyl acetamide)). Then 0.2 ml of Solution B was applied. (Solution B contained 30% 8KL5, 20 mg/ml Ferrous Ammonium Sulfate hexahydrate (Aldrich), 3% fructose, and 0.3% NVMA. Cure was instantaneous, and no discoloration of the gel occurred. The bond held during overnight soaking in distilled water.

EXAMPLE 18

Sprayed redox system.

Using the above solutions, and with monomer concentrations varying from 5% to 10% in solution A and 10% to 30% in solution B, primer (solution A) was sprayed on semivertical surfaces, followed by solution B. Surfaces were the palm of the experimenter's hand, and petri dishes. The spraying procedure caused some foaming, but gels were formed on all surfaces. Because of running of the solutions down the surfaces, gels were thicker at the bottom but present throughout. In a similar experiment, the monomer 8KTMC, containing trimethylenecarbonate biodegradable linkages between the polyethylene glycol and the acrylate cap, seemed to adhere somewhat better than the 8KL5.

EXAMPLE 19

Comparison of peroxygen compounds.

Reductant solutions contained 10% 8KL5 monomer and 8% by volume of a ferrous lactate solution, which itself contained 1% ferrous lactate and 12% fructose by weight in water. Oxidant solutions contained 10% 8KL5 monomer and a constant molar ratio of oxidizer, which was, per ml of macromer solution, 10 microliters 30% hydrogen peroxide; 8.8 microliters tert-butyl peroxide; 15.2 microliters cumene peroxide; or 0.02 g potassium persulfate. 0.5 ml of reductant was mixed with 0.25 ml oxidizer, and time to gelation was noted. With hydrogen peroxide, gelling was nearly instantaneous, while with the others there was a short delay—about 1 second—before gelation. Doubling the t-butyl peroxide concentration also produced nearly instantaneous gelling. Hydrogen peroxide produced more bubbles in the gel than the others; persulfate had almost no bubbles. The bubbles in hydrogen peroxide may come directly from the reactant, as the other compounds have different detailed mechanisms of radical formation.

EXAMPLE 20

Effect of reducing sugars.

Using the procedures of example 19, the concentration of ferrous ion was reduced to 50 ppm, and the fructose was omitted. At 100 ppm HOOH in the oxidizing solution, gel time was increased to 3 to 4 seconds, with both Fe-gluconate and Fe-lactate, but gels were yellow. Addition of 125 ppm ascorbic acid to the reducing solution prevented the formation of the yellow color.

EXAMPLE 21

Sodium gluconate addition.

It was found that raising the pH of the iron-peroxide system from 3.7 to 5.7 by addition of sodium gluconate had no effect on gelation time.

EXAMPLE 22

Compatibility with ultraviolet photoinitiators.

Solution A contained 1 g 8KL5, 0.4 ml of a ferrous lactate solution (containing 0.4 g ferrous lactate and 4.8 g of fructose in a final volume of 40 ml of distilled water), and 8.6 g of distilled water. Solution B contained 1 g of 8KL5, 0.1 ml of 30% hydrogen peroxide, and 8.9 g water. Drops of A were allowed to fall into a solution of B, resulting in drops of gel which gradually accumulated at the bottom of the solution. If solution B was supplemented with 4% by volume of a solution of 0.2 g of Irgacure™ 651 photoinitiator dissolved (with heating) in 4 ml of Tween™20 detergent, then after making bead droplets as before, the entire solution could be gelled by application of UV light. This demonstrates the compatibility of the redox and UV-curing systems. Moreover, it would be possible to make the redox-cured droplets from a monomer which would degrade either faster or slower than the continuous-phase gel, as desired, thereby potentially creating a macroporous gelled composite.

EXAMPLE 23

Relative adherence of gels.

Various gel formulas were compared in their ability to stick to domestic ham, versus their ability to adhere the fingers of the hand together. It was found that adherence of a formula to one type of surface was only weakly predictive, at best, of the adherence to the other. In another experiment, it was found that persulfate-catalysed gels are less adherent to tissue than comparable t-butyl peroxide gels, but are relatively more adherent to metal. Thus, the optimal formulation may well depend on what is to be coated with gel.

EXAMPLE 24

Intra-pleural sealing.

A source of morbidity in lungs is tie formation of bullae, which are sacs formed by separation of the plerua from the lung parenchyma. As a model for possible repair of bullae, the pleura of a detached lung was repeatedly nicked to generate small air leaks. Then a solution containing 15% of 35KL18 macromer, 20 ppm of eosin, 5 milligrams/ml vinylcaprolactam, and 90 mM triethanolamine was injected between the pleura and parenchyma at the sites of the air leaks. The solution spread preferentially between the tissue layers, forming a blister-like structure. The area was transilluminated from the pleural side with is blue-green light for 40 seconds. A flexible gel was obtained, and the air leaks were sealed.

A similar procedure could be applied to other layered tissues to stop leaks and effusion. Because the gel is confined within the tissue, adherence to tissue is not a primary concern. There are a number of anatomical structures having layered tissue structures suitable for this method of sealing a tissue against leakage. Such tissue layers include the meninges, including the dura, the pia mater and the arachnoid layer; the synovial spaces of the body including the visceral and pareital pleurae, the peritoneum, the pericardium, the synovia of the tendons and joints including the bursae, the renal capsule, and other serosae; and the dermis and epidermis. In each case, a relatively fragile structure can be sealed by injection of a polymerizable fluid between adjacent layers, followed by polymerization. Formation of a biodegradable, biocompatible gel layer by non-intrusive processes such as photopolymerization is especially desirable, because it minimizes trauma to the tissue.

EXAMPLE 25

Sealing of an Injured Artery.

In an anesthetized pig, a 1.5 cm lengthwise incision was made in a carotid artery. The incision was closed with interrupted sutures, so that blood seepage occurred. The injured area was rinsed with saline, and the blood was suctioned from the treatment zone. The treatment zone was primed with 1 mg/ml eosin in buffer (TEOA in ⅓ normal phosphate buffered saline). A macromer solution was applied with a small paintbrush to the treatment zone under illumination with blue-green argon ion laser light. In a first artery, the macromer solution contained 15% 35KC3.3, 4 mg/ml N-vinylcaprolactam, and 20 ppm eosin. In a second artery, the macromer was type 35KL18, and the macromer solution has a paste-like consistency. Four applications (0.5 to 1.0 ml each) were required to seal all leaks. It was easier to build thickness with the paste-like monomer. The pig was held under anesthesia for an hour, and the injury sites were reexamined and found to be still sealed.

EXAMPLE 26

Adherence of coating layers to living tissue surfaces.

An experiment was performed to evaluate the acute adherence of a formulation of 20% macromer 35KT8A2. with redox/eosin primer to uninjured tissue in situ. An immature pig (est. 35 kg) was maintained in an anesthetized condition and various tissues and prosthetic implants (described below) were surgically exposed or prepared. Care was taken to prevent injury to the tissues; however, the dissection of connective tissue often resulted in a roughened surface where the primer/polymer was applied.

The primer and macromer were applied with separate paint brushes, and light was delivered from a bare 2 mm diameter optical fiber. The light source was periodically checked and consistently emitted approx. 580 mW of visible light through the course of the experiment at the distal tip of the delivery fiber.

The acute adherence was graded on a 1–4 scale, where 3 or better is considered acceptable: "4": cohesive failure into small pieces when the deposited gel is gripped with blunt tweezers and pulled perpendicular and/or parallel to the tissue surface.

"3": cohesive failure with larger fragments.

"2": combined cohesive/adhesive failure.

"1": adhesive failure, gel lifts off in continuous film.

A. Adherence to tissues (Tissue/adherence grade):
1) Lower stomach (proximal to pylorus)—3.5 The stomach was reexamined after 1 hour indwelling—<3.5. Still adherent, but less than at time=0. Tear strength deteriorated.
2) Common bile duct—3.5.
3) Urinary bladder—3.8 (Punctate bleeding was noted on the bladder; it was confirmed that the causes were brushes and manipulation).
4) Ureter—3.5–3.8;
5) Large bowel (descending colon 8 cm anterior to pubic bone)—4.0
6) Esophagus—3.5.
7) Patellar tendon (2 cm proximal to tibial attachment)—3.5
8) Cartilage (trochlea groove of knee)—2.5 This tissue didn't stain with eosin; polymerized gel peeled off in sheets. Removal of upper hyaline layer, deep enough for minor blood oozing to appear, improved score to 2.8.

B. Adherence to other implantable materials.:
9) Collagen coated Dacron patch—3 This was a Datascope woven Dacron graft material 8 mm diameter. Collagen impregnated; 6-0 Prolene sutures.

10) Abdominal aortic graft—3.5. This was a Meadox Dacron double velour (inside/outside); 6 mm Inside diameter; Cat No. 174406. Lot No 245246.Sterilized 1986. The graft was preclotted in autologous blood. The animal was heparinized before implantation.
11) Gore FEP (fluorinated ethylene propylene) in vitro test—0. Material would not stain; cured polymer slid off without effort.
12) Carotid Gore patch—2.5–3. Polymer adhered to sutures and surrounding tissue.
13) Hernia mesh—2.5 (more or less). Polymer was. used to anchor the mesh (by U.S. Surgical) onto external abdominal oblique fascia. The polymer was suitable for positioning, but did not provide "structural" anchoring.

EXAMPLE 27

Process for sealing medical devices to body tissues

There is a need to seal or bond medical device surfaces to tissue. To be successful, this application requires the sealant or adhesive to form strong bonds to both the device and the tissue. Important examples of this application apply to sustained use devices such as percutaneous catheters (e.g. central venous catheters), percutaneous cannulae (e.g. for ventricular assist devices), urinary catheters, percutaneous electrical wires, ostomy appliances, electrodes (surface and implanted) and the like. In such devices, there is a tendency of the implant or device to move relative to the surrounding tissue. Such movement can allow entry of microorganisms, or can intensify the reaction of the tissue to the implant. Moreover, when a device is inserted percutaneously, then during the process of healing the epidermis in contact with the implant may undergo "marsupialization", or the formation of a partial pouch along the surface of the implant. This can retard healing of the percutaneous opening, following removal of the device.

In scope, the process includes sealing the device/tissue interface for any medical device that crosses or disrupts a tissue layer whose continuity provides a natural defense mechanism against infection or bodily fluid loss (skin, mucous membranes). This technology is also applicable to obliterating potential space between implanted devices that do not allow tissue ingrowth/ongrowth and the implant bed, serving to reduce device movement which is a cause of chronic inflammation. These tissue-device sealants may also serve as matrices for drug delivery, for example the delivery of antimicrobials to prevent infection.

Bioabsorbable hydrogels and non-absorbable analogs are appealing for these applications in that they may be formed in place to seal (or "caulk") around the device. Hydrogels usually adhere poorly to hydrophobic device surfaces which comprise most of the examples listed above.

However, a process is provided herein which produces a strong attachment of hydrogel to a hydrophobic surface during in situ polymerization of hydrogel components. It involves applying a primer containing adequate concentrations of an initiator of polymerization (Eosin Y and/or other ingredients) to a hydrophobic surface (in the example below, polystyrene, in a 12 well plate) following with a sealant composition based on a polymerizable macromer (in this example containing triethanolamine co-initiator), and effecting polymerization. The different embodiments, 27.1–27.3, are described below.

27.1: Into one well of a 12 well microtiter dish was placed 0.1 ml of a primer solution containing 500 ppm eosin with ferrous gluconate (5 mg/ml), fructose(10 mg/ml), and macromer 3.3KL5A2 (30%). Then 0.9 ml was added of a solution containing 12.8% of macromer F127T4A2 (i.e., poloxamer Pluronic F127, with 4 units of trimethylene carbonate and acrylate end caps), 125 ppm t-butyl peroxide, 90 mM triethanolamine and 0.4% VC (N-vinylcaprolactam). The mixture partially gelled on mixing, but the gel was not coherent. After illumination with blue light for 2×20 sec., a coherent gel was formed. However it was not tightly adhered to the surface of the plastic.

27.2: The experiment was repeated, but the eosin concentration was raised to 2000 ppm. Initially the solution did not gel as well, but on illumination the gel adhered strongly to the plastic.

27.3: The experiment was repeated at 2000 ppm eosin concentrations, but without the "redox" components (ferrous gluconate, fructose, t-butyl peroxide). Adherence was stronger at 2000 ppm eosin (alone) than at 500 ppm even with redox materials, although not as strong as with the redox components present.

The results are compatible with the idea that the eosin was absorbing to the surface of the plastic during the course of the experiment. To validate this, a solution containing 12.8% macromer (F127T4A2), the usual VC and buffer, no redox components, and 2000 ppm eosin was applied to a well and allowed to stand for about 10 seconds. The gel was strongly adherent. In a comparable experiment at 100 ppm eosin, the gel was formed but adhered weakly.

Thus, a critical variable here appears to be the level of photoinitiator—here eosin—in the primer. Relatively high concentrations (2000 ppm) gave stronger bonds of hydrogel to polystyrene than lower amounts. The use of "redox" coinitiators gave stronger gels, but high Eosin levels gave strong bonds with or without "redox" coninitiation.

In other experiments, it was demonstrated that the system that gave the strongest bonds to the polystyrene also gave very strong bonds to animal tissue (cadaveric goat gingiva). The strong bonding of sealant to polystyrene 12 well plates may thus used (in the absence of tissue)to demonstrate the tissue bonding capability of a particular hydrogel, thus minimizing experimentation. This system, applied simultaneously to a tissue and a hydrophobic device (via application of primer, sealant, and light) would thus appear to result in an effective tissue-to-device sealant with wide-ranging applicability.

EXAMPLE 28

Use of redox-assisted photoinitiation in treatment of injured arteries.

The interior of a rabbit carotid artery was injured by scraping with an inflated balloon catheter. The injured area was then isolated with a two balloon catheter, and the injured zone was flushed with saline;stained on its surface with an initiator solution, containing 20 ppm eosin Y in PBS (phosphate-buffered saline, pH 7.4);further flushed with saline to remove unbound eosin;treated with a buffered solution containing 90 mM TEOA (triethanolamine), pH 7.4; 30% by weight of polymerizable macromer; 0.2% to 0.25% of vinylpyrrolidone or vinylcaprolactam; and optionally 50 ppm of ferrous sulfate. The treatment zone was then exposed to 100 mW/sq. cm.of green light from an argon laser for 20 seconds. The balloons were collapsed and blood flow was permitted to resume, resulting in flushing of excess macromer from the zone into the rest of the circulation. In various tests, it was found that a thin layer of gel was formed on the inside of the artery both with and without the addition of ferrous ion. It was further found that the layer persisted for longer times in the presence of the ferrous ion.

To better understand this system, gels were formed in test cells, and their mechanical properties after various lengths of illumination were compared. It was found that the addition of iron resulted in gels which were better cured and which were relatively less sensitive to the exact concentration of other reagents, or to the duration of illumination. This is shown in more detail in Table 3:

TABLE 3

| | Ratio of Modulus at 20 sec. to 90 sec. of illuminatian | | |
|---|---|---|---|
| Illumination | Redox conc. | 20 ppm eosin | 100 ppm eosin |
| 100 mW/cm2 | 50 ppm Fe | 93% | 83% |
| | 0 ppm Fe | 63% | 14% |
| 400 mW/cm2 | 50 ppm Fe | 98% | 77% |

Conditions: 30% 3.3KL5 in 90 mM TEOA pH 7.4 and 2 μL VP/mL

The ratio of the gel modulus at 20 sec. illumination to 90 seconds is a measure of the rapidity of complete polymerization of the gel. Higher numbers denote faster polymerization. It can be seen that the addition of iron markedly accelerates the cure, and that this effect is more pronounced at 100 ppn eosin, where the underlying variation is greater, and likewise at lower light levels.

EXAMPLE 29

Redox systems with Urethanes, Acids and Amides, using Ceric Ion.

The objective of the experiment was to determine the feasibility of making polar-ionic macromers using a Ce-IV based redox system with urethanes, carboxylates or amides as reductant. A special macromer was made (3.3KL5A1: 3.3K PEG; 5 lactides; 1 acrylate) and end-capped with diisocyanate to form a urethane by standard procedures.

The different embodiments, 29.1–29.4, are described below.

29.1: Add 1 ml of methacrylic acid to 10 ml of 2.25 wt. % Ceric ammonium nitrate in water ("Ce solution"; has yellow color). A white precipitate was formed immediately; the yellow color faded over time.

29.2: Add 10 ml Ce solution to a 10 ml solution containing 0.5 ml acetic acid and 0.5 ml methyl acrylate. A white precipitate formed immediately, and the yellow color gradually faded.

29.3: Add 1 g of the NCO-end capped initiator to 10 ml of Ce solution, and mix with 10 ml of a 50% w/v solution of AMPS (acrylamido methyl propanesulfonic acid). The solution remained yellow and unprecipitated. However, after standing overnight at room temperature the solution had become colorless and highly viscous, and was not filterable through a 0.2 micron filter. This suggests a high degree of polymerization, perhaps with some crosslinking.

29.4: A carboxylate-terminated macromer was made by treating 3.3KL5A1.0 with succinic anhydride. The purified reprecipitated polymer was dissolved in deionized water (0.39 g /7 ml) and 2.0 g of AMPS was added. The pH was adjusted to 3.8 with NaOH. Then 55 mg. of Ce(IV) ammonium nitrate was added (approximately stoichiometric with the expected number of carboxyl groups). The volume was adjusted to 10 ml. with water. The solution rapidly became turbid and increased in viscosity, and appeared to be crosslinked to a gel within about 1 hr. The resulting gel could be dissolved by pH 13 NaOH solution in about 1 hr., showing that the crosslinks involved the degradable ester moieties.

It appeared that both carboxylic groups and urethane groups can serve as reductants for ceric ion in a redox-catalysed polymerization of an unsaturated group. Other groups known to be effective in such reactions can also be used where the conditions are physiologically reasonable.

EXAMPLE 30

Adherence of medical device material to tissue.

In this example, direct adhesion of a typical medical polymer to tissue is demonstrated. It is further shown that the location of the plane of fracture of the composite can be controlled by selection of concentration and type of photoinitiator.

Microscope-slide-sized pieces of Pellethane (Dow) extruded polyurethane sheet were washed with acetone to remove impurities and dried in a vacuum oven. They were then stained with a solution of 2000 ppm Eosin Y in PBS, as above, for several minutes until pink staining of the polyurethane was observed. Sheets were rinsed in water and air dried.

Pieces of abdominal wall were excised from a euthanized rat, and used with the peritoneal side "up" ("tissue"). Tissue was clamped to a glass slide with binder clips. Thin Teflon spacers were placed on top of the tissue. Dried sheets of urethane were clamped into the sandwich, eosin-stained side towards the tissue, forming a thin chamber between the polyurethane and the tissue, typical of clearances found in medical practice. Four combinations of solutions were tested.

The different embodiments, 30.1–30.4 are described below.

30.1: About 0.2 ml of a primer solution containing 2000 ppm eosin in PBS was infused into the chamber, and was removed by wicking after about a minute. A macromer solution (about 0.2 ml) was added, containing 12.8% F127T4A2 macromer (as in example 27), 90 mM TEOA and 0.4% VC (vinyl caprolactone), and, in this experiment, 2000 ppm eosin. The chamber was transilluminated through the glass slide and rat flap for 40 seconds. The macromer did not completely polymerize, and on removal of the clamps the tissue separated from the urethane without appreciable force.

30.2: The above experiment was repeated, but the eosin concentration in the macromer solution was reduced to 20 ppm. Polymerization was complete. On separation of the tissue from the urethane, the gel fractured while remaining adherent to both tissue and to the urethane.

30.3: The above experiment 30.2 was repeated, except that the redox accelerator t-butyl peroxide was present in the macromer solution at 125 ppm, and the primer contained Ferrous gluconate and fructose as in Example 27.1. The gel was completely polymerized. On attempting to peel the tissue from the urethane, the tissue tore—i.e., both the gel and its bonds, to both tissue and device, were stronger than the tissue itself.

30.4: Experiment 30.2 was repeated, except that the concentration of eosin in the primer was reduced to 20 ppm. Polymerization was complete. On peeling the tissue, failure of adhesion occurred at the interface between the gel and the tissue.

This example demonstrates that by selection of initiator types and concentrations, the fracture plane of a device bonded to a tissue by a gel can be varied at will, and behaves in a reasonable and predictable way. Although the gel compositions in this example were degradable, the peeling was done at short times, and the results will extrapolate directly to non-degradable gels.

Modifications and variations of the present invention will be obvious to those skilled in the art. Such modifications and variations are intended to come within the scope of the appended claims.

We claim:

1. A process for reducing leakage of bodily fluids comprising:

applying a polymerization initiator to an area of a tissue surface, applying a solution containing a biodegradable, biocompatible, polymerizable monomer to the initiator-coated surface in an initiator-incorporating manner; and polymerizing the monomer to seal the area and to reduce leakage of the bodily fluids through the area.

2. The process of claim 1 in which the bodily fluid is selected from the group consisting of blood, serum, air, urine, bowel contents, cerebrospinal fluid, tears, and mucus.

3. The process of claim 2 in which the fluid is air.

4. The process of claim 2 wherein the body area is part of the respiratory tract.

5. The process of claim 4 wherein the body area is a lung.

6. The process of claim 1 wherein the polymer is photopolymerizable and the initiator is a photoinitiator.

7. The process of claim 6 wherein the photoinitiator is an eosin.

8. The process of claim 1 in which the area to be treated is coated with a photoinitiator, and the polymerizable monomer is applied in a solution containing a photoinitiator.

9. The process of claim 1 in which the tissue surface is the surface between two tissue layers which are adhered together when the material is polymerized.

10. The process of claim 9 where the tissue layers are selected from the meninges, the synovial spaces of the body, the peritoneum, the pericardium, the synovia of the tendons and joints, the serosae, and the dermis and epidermis.

11. The process of claim 4 in which the solution further comprises biologically active materials for release to the tissue.

12. The process of claim 11 in which the biologically active substance is selected from the group consisting of proteins, peptides, organic synthetic molecules, inorganic compounds, natural extracts, nucleic acids, lipids, steroids, carbohydrates, and combinations thereof.

13. The process of claim 9 in which the body area is selected from the site of an anastomosis, a suture, a staple, a puncture, an incision, a laceration, and an apposition of tissue.

14. The process of claim 1 further comprising applying additional polymer layers onto the first polymer coating layer, wherein the concentration of the polymerizable material in the solution used to prepare the first layer is higher than the concentration of polymerizable material in the solutions used to prepare the additional layers.

* * * * *